United States Patent
Ziegler et al.

[11] Patent Number: 5,863,951
[45] Date of Patent: Jan. 26, 1999

[54] N-(ORTHO-SUBSTITUTED BENZYLOXY) IMINE DERIVATIVES AND THEIR USE AS FUNGICIDES, ACARICIDES OR INSECTICIDES

[75] Inventors: Hugo Ziegler, Witterswil, Switzerland; Stephan Trah, Freiburg, Germany; René Zurflüh, Basel, Switzerland

[73] Assignee: Novartis Finance Corporation, New York, N.Y.

[21] Appl. No.: 809,985

[22] PCT Filed: Sep. 26, 1995

[86] PCT No.: PCT/EP95/03802

§ 371 Date: Apr. 3, 1997

§ 102(e) Date: Apr. 3, 1997

[87] PCT Pub. No.: WO96/11183

PCT Pub. Date: Apr. 18, 1996

[30] Foreign Application Priority Data

Oct. 7, 1994 [CH] Switzerland .............. 3033/94

[51] Int. Cl.⁶ .......... A01N 33/24; A01N 37/12; C07C 249/00; C07C 229/00
[52] U.S. Cl. .......... 564/640; 514/538; 564/254; 564/256; 560/35
[58] Field of Search ............. 564/254, 256; 514/640, 538; 560/35

[56] References Cited

U.S. PATENT DOCUMENTS

| | | | |
|---|---|---|---|
| 5,104,872 | 4/1992 | Tsubata et al. | 514/238.2 |
| 5,238,956 | 8/1993 | Clough et al. | 514/506 |

FOREIGN PATENT DOCUMENTS

| | | |
|---|---|---|
| 9177782 | 6/1983 | Australia . |
| 4193793 | 1/1994 | Australia . |
| 1454695 | 8/1995 | Australia . |
| 0414153 | 2/1991 | European Pat. Off. . |
| 9007493 | 9/1990 | WIPO . |
| 9518789 | 7/1995 | WIPO . |

OTHER PUBLICATIONS

International Search Report, PCT/EP95/03802, (1996).

*Primary Examiner*—Deborah C. Lambkin
*Attorney, Agent, or Firm*—Hesna J. Pfeiffer

[57] ABSTRACT

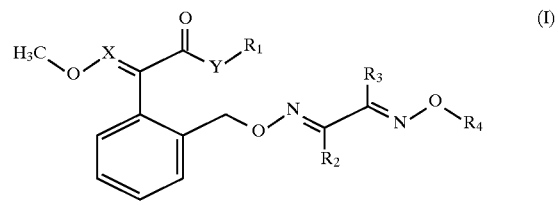

The present invention relates to oxime ethers of general formula (I) and to their isomers and isomer mixtures which are possible in which (a) X is an N atom and Y is an oxygen atom or NH, or (b) X is CH and Y is an oxygen atom, in which furthermore $R_1$ is $C_1$–$C_4$ alkyl; $R_2$ is hydrogen, $C_1$–$C_4$ alkyl cyclopropyl or cyano; $R_3$ is cyano, substituted or unsubstituted $C_1$–$C_6$ alkoxycarbonyl, substituted or unsubstituted di($C_1$–$C_6$ alkyl)aminocarbonyl, substituted or unsubstituted $C_1$–$C_6$ alkyl-S(O)$_n$, substituted or unsubstituted aryl-S(O)$_n$, substituted or unsubstituted heteroaryl, substituted or unsubstituted heterocyclyl or substituted or unsubstituted heterocyclylcarbonyl; and $R_4$ is $C_1$–$C_6$ alkyl; $C_1$–$C_6$ haloalkyl having 1 to 5 halogen atoms; $C_1$–$C_4$ alkoxy-$C_1$–$C_2$ alkyl; $C_2$–$C_6$ alkenyl which is unsubstituted or substituted by 1 to 3 halogen atoms; $C_3$–$C_6$ alkynyl; $C_3$–$C_6$ cycloalkyl-$C_1$–$C_4$ alkyl which is unsubstituted or substituted by 1 to 4 halogen atoms, and n assumes a value of 1 or 2. These compounds can be used in the form of crop protection products for controlling plant diseases, insects and pests from the order Acarina.

18 Claims, No Drawings

N-(ORTHO-SUBSTITUTED BENZYLOXY) IMINE DERIVATIVES AND THEIR USE AS FUNGICIDES, ACARICIDES OR INSECTICIDES

This application is a 371 of PCT/EP95/03802 Sep. 26, 1995.

The present invention relates to oxime ethers of the general formula I

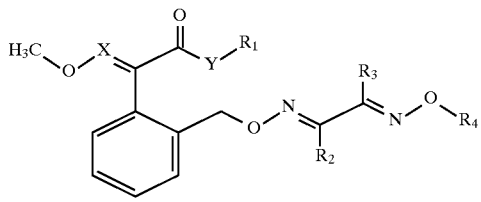

and to their isomers and isomer mixtures which are possible in which a)
 X is an N atom and
 Y is an oxygen atom or NH, or
b)
 X is CH and
 Y is an oxygen atom,
in which furthermore
 $R_1$ is $C_1$–$C_4$alkyl;
 $R_2$ is hydrogen, $C_1$–$C_4$alkyl, cyclopropyl or cyano;
 $R_3$ is cyano, substituted or unsubstituted $C_1$–$C_6$alkoxycarbonyl, substituted or unsubstituted di($C_1$–$C_6$alkyl)aminocarbonyl, substituted or unsubstituted $C_1$–$C_6$alkyl-S(O)$_n$, substituted or unsubstituted aryl-S(O)$_n$, substituted or unsubstituted heteroaryl, substituted or unsubstituted heterocyclyl or substituted or unsubstituted heterocyclylcarbonyl; and
 $R_4$ is $C_1$–$C_6$alkyl; $C_1$–$C_6$haloalkyl having 1 to 5 halogen atoms; $C_1$–$C_4$alkoxy-$C_1$–$C_2$alkyl; $C_2$–$C_6$alkenyl which is unsubstituted or substituted by 1 to 3 halogen atoms; $C_3$–$C_6$alkynyl; $C_3$–$C_6$cycloalkyl-$C_1$–$C_4$alkyl which is unsubstituted or substituted by 1 to 4 halogen atoms, and
 n assumes a value of 1 or 2.

The compounds according to the invention have fungicidal, acaricidal and insecticidal properties and are suitable as agrochemical active ingredients for use in agriculture.

The invention furthermore relates to a process for the preparation of the compounds according to the invention and to fungicidal, acaricidal and insecticidal compositions which comprise such compounds as active ingredients, and to the use of such compounds and compositions for controlling phytopathogenic fungi, Acarina and insects, and for preventing such an attack.

If asymmetric carbon atoms exist in the compounds of the formula I, the compounds occur in optically active form. In any case, the compounds will be present in [E] and/or [Z] forms merely owing to the presence of the aliphatic and the oximino double bonds. Atropisomerism may furthermore occur. The formula I is intended to embrace all these isomeric forms which are possible and also their mixtures, for example racemic mixtures and any [E/Z] mixtures.

Depending on the number of the carbon atoms, alkyl and alkoxy groups are straight-chain or branched and are, for example, methyl, ethyl, n-propyl, isopropyl, n-butyl, sec-butyl, isobutyl, tert-butyl, n-pentyl, neopentyl, sec-pentyl, tert-pentyl, n-hexyl and the like.

Cycloalkyl is to be understood as meaning cyclopropyl, cyclobutyl, cyclopentyl or cyclohexyl.

Alkenyl is to be understood as meaning straight-chain or branched alkenyl, for example vinyl, 1-methylvinyl, allyl, 1-butenyl, isopropenyl.

Alkynyl is, for example, ethynyl, 1-propynyl or 1-butynyl.

Halogen is fluorine, chlorine, bromine or iodine, preferably fluorine, chlorine or bromine.

Haloalkyl can have identical or different halogen atoms.

Substituents of the substituted alkoxycarbonyl, dialkylaminocarbonyl and alkyl-S(O)$_n$ groups are, inter alia, 1 to 5 halogen atoms, cyano, methoxy, methylthio, cyclopropyl, alkenyl, alkynyl, phenyl.

Substituents of the substituted aryl-S(O)$_n$, heteroaryl and heterocyclyl groups are, inter alia, $C_1$–$C_4$alkyl, halogen, cyano, nitro, $C_1$$C_4$alkoxy, $C_1$–$C_4$alkylthio, halo-$C_1$–$C_2$alkyl, halo-$C_1$–$C_2$alkoxy, $C_1$–$C_4$alkoxycarbonyl.

1 to 3 substituents may exist independently of one another.

Aryl is phenyl or naphthyl, preferably phenyl.

The term heteroaryl includes furan, pyrrole, and aromatic 5-membered rings having two to three and six-membered rings having one to three identical or different hetero atoms N, O or S, all of which can be benzo-fused, and also the radical benzothienyl. Other individual examples which may be mentioned are pyridine, pyrimidine, pyrazine, thiazole, oxazole, isoxazole, isothiazole, triazine, quinoline, isoquinoline, pyridazine, pyrazole, imidazole, quinazoline, quinoxaline, benzimidazole, benzofuran, indole, isoindole, benzothiazole, thiadiazole.

The term heterocyclyl represents 5- to 7-membered rings which have 1–3 identical or different hetero atoms N, O and/or S. Examples are $\Delta^2$-oxazoline, $\Delta^2$-thiazoline; 5,6-dihydro-4H-1,3-thiazine; 5,6-dihydro4H-1,3-oxazine, and furthermore pyrrolidine, piperidine, morpholine, 4-alkylpiperidine, azepine.

Preferred within the scope of the invention are the following combinations of substituents:
1) Compounds of the formula I in which:
 X is CH or N
 Y is O
 $R_1$ is methyl or ethyl
 $R_2$ is methyl, cyclopropyl or cyano and
 $R_3$ and $R_4$ are as defined for formula I.
2) Compounds of the formula I in which:
 X is N
 Y is NH
 $R_1$ is methyl, ethyl or isopropyl,
 $R_2$ is methyl, cyclopropyl or cyano and
 $R_3$ and $R_4$ are as defined for formula I.
3) Compounds of the formula I in which:
 $R_1$ is methyl
 $R_2$ is methyl
 $R_4$ is $C_1$–$C_6$alkyl, while
 X, Y and $R_3$ are as defined for formula I.
4) Compounds of the formula I in which:
 $R_1$ is methyl
 $R_2$ is methyl
 $R_3$ is cyano, substituted or unsubstituted $C_1$–$C_6$alkoxycarbonyl or substituted or unsubstituted di($C_1$–$C_6$alkyl)aminocarbonyl or substituted or unsubstituted heterocyclylcarbonyl and
 X, Y and $R_4$ are as defined for formula I.

5) Compounds of the formula I in which:
R$_1$ is methyl
R$_2$ is methyl
R$_3$ is substituted or unsubstituted C$_1$–C$_6$alkyl-S(O)$_n$, substituted or unsubstituted aryl-S(O)$_n$, substituted or unsubstituted heteroaryl or substituted or unsubstituted heterocyclyl, and
n is 1 or 2, while
X, Y and R$_4$ are as defined for formula I;
and amongst these
6) those compounds of the formula I in which:
R$_3$ is substituted or unsubstituted heterocyclyl or substituted or unsubstituted heteroaryl,
R$_4$ is C$_1$–C$_6$alkyl, C$_1$–C$_6$haloalkyl having 1 to 5 halogen atoms, or C$_3$–C$_6$cycloalkyl-C$_1$–C$_4$alkyl which is unsubstituted or substituted by 1 to 4 halogen atoms, and
R$_1$, R$_2$, X and Y are as defined above.
7) Compounds of the formula I in which:
R$_1$ is methyl
R$_2$ is methyl
R$_3$ is substituted or unsubstituted C$_1$–C$_6$alkoxycarbonyl or substituted or unsubstituted heterocyclyl,
R$_4$ is C$_1$–C$_6$alkyl, C$_1$–C$_6$haloalkyl, or C$_3$–C$_6$cycloalkyl-C$_1$–C$_4$alkyl which is unsubstituted or substituted by 1 to 4 halogen atoms, and
X and Y are as defined for formula I.
8) Other preferred compounds of the formula I are those in which the X=C double bond is in the E form. This preference also applies to all sub-groups which are mentioned individually.

A) To prepare a compound of the formula I in which X, Y, R$_1$, R$_2$, R$_3$ and R$_4$ are as defined for formula I, the following procedure may be used.

An oxime of the general formula II

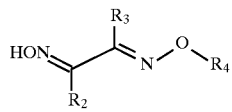

in which R$_2$–R$_4$ are as defined above is allowed to react with a benzyl derivative of the general formula III

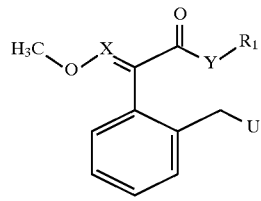

in which R$_1$, X and Y are as defined above and U is a leaving group.

This reaction is a nucleophilic substitution which can be carried out under the relevant customary reaction conditions. The leaving group U in the benzyl derivative of the formula III is preferably to be understood as meaning chlorine, bromine, iodine, mesyloxy, benzenesulfonyloxy, nitrobenzenesulfonyloxy or tosyloxy. The reaction is expediently carried out in an inert organic diluent, such as a cyclic ether, for example tetrahydrofuran or dioxane, acetone, dimethylformamide or dimethyl sulfoxide, in the presence of a base, such as sodium hydride, sodium carbonate, potassium carbonate, sodium amide, a tertiary amine, for example a trialkylamine, in particular diazabicyclononane or diazabicycloundecene, or silver oxide, at temperatures between −20° C. and +80° C., preferably within a temperature range of from 0° C. to 50° C.

Alternatively, the reaction can be carried out under phase transfer catalysis in an organic solvent, for example methylene chloride, in the presence of an aqueous basic solution, for example sodium hydroxide solution, and of a phase transfer catalyst, for example tetrabutylammonium hydrogen sulfate, at room temperature.

B) To obtain a compound of the formula I where Y is NH(C$_1$–C$_4$alkyl), the basic compound of the formula I in which Y is OCH$_3$ is reacted, for example, with C$_1$–C$_4$alkylamine, for example methylamine. The reaction is expediently carried out in ethanol, which is already used as the solvent for alkylamine, at temperatures between 0° C. and 40° C., preferably at room temperature.

The resulting compounds of the formula I can be isolated and purified by methods known per se. Resulting isomer mixtures, for example E/Z isomer mixtures, can be separated into the pure isomers by methods which are also known per se, for example by chromatography or fractional crystallization.

The oximes of the general formula II which are used as starting materials are prepared by reacting a ketone of the general formula IV

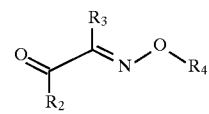

with hydroxylamine or a salt thereof, for example the hydrochloride. The reaction is expediently carried out in pyridine or methanol as the solvent, a base being required if methanol is used, for example an alkali metal carbonate, such as potassium carbonate, a tertiary amine, such as triethylamine or diazabicyclononane, pyridine or silver oxide, at temperatures between −20° C. and +80° C. or the boiling point of methanol, preferably in a temperature range of from 0° C. to 50° C.

The invention also relates to the novel oximes of the formula II in which R$_2$, R$_3$ and R$_4$ are as defined for formula I.

The ketones of the general formula IV are either known or can be prepared by known methods (for example EP 324 418 and EP 325 183 (Takeda Chem. Ind.); EP 416 857 (Wako Pure Chem. Ind.) or: WO 87/03585 (MECT Corp.) and G. Ponzio, G. Bertini, Gazz. 61, 51 (1931) for the synthesis of a direct precursor of IV).

The starting materials of the formula III can also be prepared in a manner known per se, for example as described in European Patent EP-A-203 606 (BASF) and in the references cited therein, or in Angew. Chem. 71, 349–365 (1959).

C) To prepare a compound of the formula I in which X, Y and R$_1$ to R$_4$ are as defined for formula I, the following procedure may be adopted:

An oxime of the general formula V

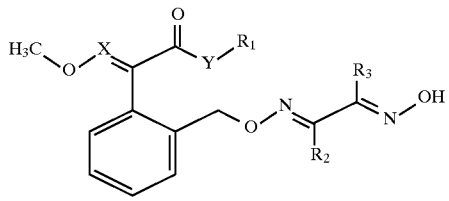

in which X, Y, R$_1$, R$_2$ and R$_3$ are as defined above is reacted with a compound of the general formula

U-R₄  VI in which R₄ is as defined under formula I and U as defined under formula III.

This reaction is a nucleophilic substitution as described under A).

D) To prepare an oxime of the formula V in which X, Y, R₁, R₂ and R₃ are as defined for formula I, a ketone of the general formula VII

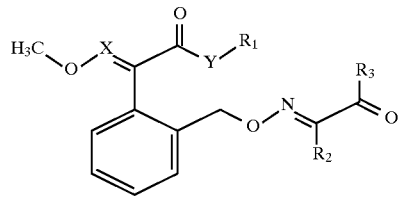

VII in which X, Y, R₁, R₂ and R₃ are as defined above can be reacted with hydroxylamine or with a salt thereof, for example the hydrochloride. This reaction is expediently carried out in pyridine or methanol as the solvent, the use of methanol requiring a base, for example an alkali metal carbonate (such as potassium carbonate), a tertiary amine (such as triethylamine or diazabicyclononane, pyridine or silver oxide), at temperatures between −20° C. and +80° C. or the boiling point of methanol, preferably in a temperature range of from 0° C. to 50° C.

The ketone of the general formula VII is prepared analogously to the method described under A). The ketones of the general formula VII and ways of obtaining them are described, for example, in EP-370 629, EP-506 149, EP-403 618, EP414 153, EP-463 488, EP472 300, EP-460 575, WO-92/18494 and in other publications.

E) A compound of the formula I in which X, Y and R₁ to R₄ are as defined for formula I can also be obtained by methylating an enol or oxime of the general formula VIII

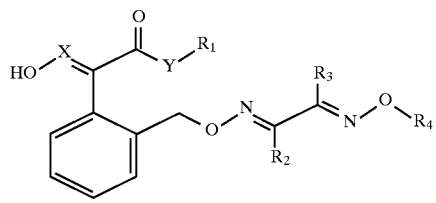

VIII in which X, Y and R₁ to R₄ are as defined above by means of a methylating agent, for example methyl iodide, dimethyl sulfate or diazomethane. The reaction is expediently carried out in the presence of a base, for example potassium carbonate or sodium hydride, in a suitable solvent and at suitable reaction temperatures (see, for example, H. S. Anker and H. T. Clarke; Organic Synthesis, Coll. Vol. 3, 172).

F) A compound of the formula VIII in which X, Y and R₁ to R₄ are as defined for formula I can also be obtained from a phenylacetic acid derivative of the formula IX

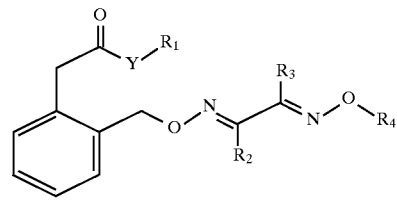

IX in which Y and R₁ to R₄ are as defined above and a formate (for example HCOOCH₃) in the presence of a base analogously to the method described in EP-A-178 826 (X═CH), or from IX by means of nitrosation with nitrous acid HONO or a nitrite in the presence of a base analogously to the method described in EP-A-254 426. A compound of the formula I can be obtained from a compound VIII by means of methylation, as described under E).

G) Another possibility of synthesizing a compound of the formula VIII is the following reaction:

A keto ester of the formula X

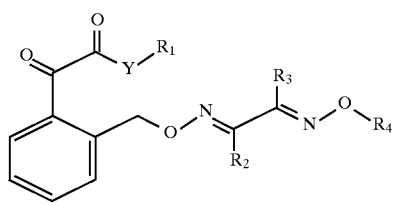

X in which Y and R₁ to R₄ are as defined for formula I is reacted with methoxymethylenetriphenylphosphorane analogously to the method described in EP-A-178 826 or with O-methylhydroxylamine (or a salt thereof) analogously to the method described in EP-A-254 426.

The novel compounds of the formulae VII, VIII, IX and X are also provided by the invention.

It has now been found that compounds of the formula I have a microbicidal spectrum which is particularly favourable for practical requirements for the control of phytopathogenic microorganisms, in particular fungi. They have very advantageous curative, preventive and, in particular systemic properties and can be used for the protection of a large number of plants. Using the active ingredients of the formula I, the pests which can be found on plants or parts of plants (fruits, flowers, foliage, stalks, tubers, roots) in various crops can be contained or destroyed, the protection against phytopathogenic microorganisms also extending to those parts of the plants which are formed at a later point in time.

The compounds of the formula I can furthermore be used as seed-dressing agents for the treatment of seed (fruits, tubers, kernels) and nursery plants to protect them against fungal infection and against soil-borne phytopathogenic fungi.

Compounds of the formula I act, for example, against phytopathogenic fungi belonging to the following classes: *Fungi imperfecti* (in particular Botrytis, Pyricularia, Helminthosporium, Fusarium, Septoria, Cercospora, Cercosporella and Alternaria); Basidiomycetes (for example Rhizoctonia, Hemileia, Puccinia); Ascomycetes (for example Venturia and Erysiphe, Podosphaera, Monilinia, Uncinula), but in particular against Oomycetes (for example Phytophthora, Peronospora, Bremia, Pythium, Plasmopara).

The compounds of the formula I according to the invention are well tolerated by warm-blooded species, fish and plants and are furthermore valuable active ingredients against insects and pests from the order Acarina as are found in useful plants and ornamentals in agriculture, horticulture and forestry. The compounds of the formula I are particularly suitable for controlling pests in cotton, vegetable, fruit and rice crops, such as spider mites, aphids, butterfly caterpillars and leaf and plant hoppers in rice. Main targets to be controlled are spider mites such as *Panonychus ulmi*, aphids such as *Aphis craccivora*, butterfly caterpillars such as those of *Heliothis virescens* and leaf and plant hoppers in rice such as *Nilaparvata lugens* or *Nephotettix cincticeps*.

The good pesticidal action of the compounds I according to the invention corresponds to a destruction rate (mortality) of at least 50–60% of the abovementioned pests.

Other fields of application of the active ingredients according to the invention are the protection of stored products and materials, the stored products being protected against rots and moulds and also against animal pests (for example grain weevils, mites, fly larvae etc.). In the hygiene sector, compounds of the formula I effect successful control against animal parasites such as ticks, mites, warble flies etc. in domestic animals and productive livestock. The compounds I are active against individual or all development stages of normally sensitive, but also resistant, species of pests. Their action may become apparent for example in a destruction of the pests, either immediately or only after some time has elapsed, for example during ecdysis, or in a reduced oviposition rate and/or hatching rate.

The action of the compounds I according to the invention and of the compositions comprising them can be broadened considerably and adapted to prevailing circumstances by adding other insecticides and/or acaricides. Suitable additives are, for example, representatives of the following classes of active ingredients: organophosphorus compounds, nitrophenols and derivatives, formamidines, ureas, carbamates, pyrethroids and chlorinated hydrocarbons.

Target crops for the use in crop protection disclosed herein are, within the scope of the present invention, for example the following plant species: cereals (wheat, barley, rye, oats, triticale, rice, maize, sorghum and related species); beet (sugar and fodder beet); pomaceous fruit, stone fruit and soft fruit (apples, pears, plums, peaches, almonds, cherries, strawberries, gooseberries, raspberries and blackberries); pulses (beans, lentils, peas, soya beans); oil crops (oilseed rape, mustard, poppy, olives, sunflowers, coconut, castor, cocoa, groundnuts); cucurbits (pumpkin, cucumbers, melons); fibre plants (cotton, flax, hemp, jute); citrus fruit (oranges, lemons, grapefruit, tangerines); vegetables (spinach, lettuce, asparagus, cabbages, carrots, onions, tomatoes, potatoes, bell pepper); Lauraceae (avocado, Cinnamonium, camphor) or plants such as tobacco, nuts, coffee, sugar cane, tea, pepper and other spice plants, grape vines, hops, eggplants, Musaceae and natural latex plants, and flowers and ornamentals.

Active ingredients of the formula I are conventionally used in the form of compositions and can be applied to the area or plants to be treated simultaneously or in succession with other active ingredients. These other active ingredients can be fertilizers, trace element mediators or other preparations which affect plant growth. It is also possible to use selective herbicides and insecticides, fungicides, bactericides, nematicides, molluscicides or mixtures of a plurality of these preparations, if desired together with other carriers conventionally used in the art of formulation, surfactants or other additives which enhance application, without adversely affecting the efficacy of the compounds of the formula I.

Suitable carriers and additives can be solid or liquid and are the substances expediently used in the art of formulation, for example natural or regenerated mineral substances, solvents, dispersants, wetting agents, tackifiers, thickeners, binders or fertilizers.

The following solvents are suitable: aromatic hydrocarbons, preferably the fractions $C_8$ to $C_{12}$, for example xylene mixtures or substituted naphthalenes, phthalic esters such as dibutyl or dioctyl phthalate, aliphatic hydrocarbons such as cyclohexane or paraffins, alcohols and glycols as well as their ethers and esters, such as ethanol, ethylene glycol, ethylene glycol monomethyl ether or -ethyl ether, ketones, such as cyclohexanone, strongly polar solvents, such as N-methyl-2-pyrrolidone, dimethyl sulfoxide or dimethylformamide, and free or epoxidized vegetable oils, such as epoxidized coconut oil or soya oil; or water.

Solid carriers which are used, for example for dusts and dispersible powders, are, as a rule, ground natural minerals, such as calcite, talc, kaolin, montmorillonite or attapulgite.

Particularly advantageous application-promoting adjuvants which may result in a greatly reduced rate of application are, in addition, natural (animal or vegetable) or synthetic phospholipids from the series of the cephalins and lecithins, which can be obtained, for example, from soya beans.

Suitable surface-active compounds are non-ionic, cationic and/or anionic surfactants which have good emulsifying, dispersing and wetting properties, depending on the nature of the active ingredient of the formula I to be formulated. Surfactants are also to be understood as meaning mixtures of surfactants.

Suitable anionic surfactants can be so-called water-soluble soaps, but also water-soluble synthetic surface-active compounds.

Soaps which may be mentioned are alkali metal salts, alkaline earth metal salts or substituted or unsubstituted ammonium salts of higher fatty acids ($C_{10}$–$C_{22}$), for example the sodium or potassium salts of oleic or stearic acid, or of natural mixtures of fatty acids which can be obtained from, for example, coconut oil or tallow oil. Other substances which may be mentioned are the fatty acid methyl taurides.

Suitable non-ionic surfactants are polyglycol ether derivatives of aliphatic or cycloaliphatic alcohols, saturated or unsaturated fatty acids and alkylphenols which can have 3 to 30 glycol ether groups and 8 to 20 carbon atoms in the (aliphatic) hydrocarbon radical and 6 to 18 carbon atoms in the alkyl radical of the alkylphenols.

Examples which may be mentioned of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Other suitable substances are fatty acid esters of polyoxyethylene sorbitan, such as polyoxyethylene sorbitan trioleate.

The cationic surfactants are mostly quaternary ammonium salts which have, as N-substituent, at least one alkyl radical having 8 to 22 carbon atoms and, as further substituents, lower, free or halogenated alkyl, benzyl or lower hydroxyalkyl radicals.

The anionic, non-ionic or cationic surfactants conventionally used in the art of formulation are known to the expert or can be found in the relevant specialist literature:

"Mc Cutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch" [Surfactants Guide], Carl Hanser Verlag, Munich/Vienna 1981.

As a rule, the agrochemical preparations comprise 0.1 to 99%, in particular 0.1 to 95%, of active ingredient of the formula I, 99.9 to 1%, in particular 99.9 to 5%, of a solid or liquid additive and 0 to 25%, in particular 0.1 to 25%, of a surfactant.

While concentrated compositions are more preferred as commercially available goods, the end user uses, as a rule, dilute compositions.

The compositions can also comprise other additives such as stabilizers, antifoams, viscosity regulators, binders, tackifiers and fertilizers, or other active ingredients for achieving specific effects.

The formulations, i.e. the compositions, preparations or products comprising the active ingredient of the formula I with or without a solid or liquid additive are prepared in a known manner, for example by intimately mixing and/or grinding the active ingredient with an extender, for example a solvent (mixture), a solid carrier, and, if desired, surface-active compounds (surfactants).

A preferred method of applying an active ingredient of the formula I, or of an agrochemical composition which comprises at least one of these active ingredients, is application to the foliage (foliar application). Frequency and rate of application depend on the danger of attack by the pathogen in question. Alternatively, the active ingredients of the formula I can reach the plant via the soil through the root system (systemic action), by drenching the locus of the plant with a liquid preparation or incorporating the substances in solid form into the soil, for example in the form of granules (soil application). In the case of paddy rice, such granules can be metered into the flooded paddyfield. Alternatively, the compounds of the formula I can be applied to seed kernels (coating), either by soaking the kernels in a liquid preparation of the active ingredient or by applying a layer of a solid preparation. In principle, any type of plant propagation material can be protected using compounds of the formula I, for example the seed, roots, the stalk, branches or shoots.

The compounds of the formula I are employed as pure active ingredients or, preferably, together with the auxiliaries conventionally used in the art of formulation. To this end, they are expediently processed in a known manner to give, for example, emulsion concentrates, spreadable pastes, directly sprayable or dilutable solutions, dilute emulsions, wettable powders, soluble powders, dusts and granules (for example by encapsulation in polymers). The application methods, such as spraying, atomizing, dusting, spreading, brushing on or pouring, and also the nature of the compositions, are selected to suit the intended aims and the prevailing circumstances. Advantageous application rates are generally 1 g to 2 kg of active ingredient (a.i.) per ha, preferably 25 g to 800 g of a.i./ha and particularly preferably 50 g to 400 g of a.i./ha. For use as seed dressing products, doses from 0.001 g to 1.0 g of active ingredient are advantageously used per kg of seed.

The examples which follow are intended to illustrate the invention in greater detail without imposing any restriction.

1. PREPARATION EXAMPLES

Example H-1

Preparation of the compound

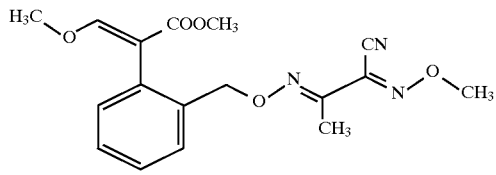

0.22 g of a 60% sodium hydride dispersion is washed with hexane and treated with 5 ml of N,N-dimethylformamide. To this suspension there are added 1.43 g of methyl 2-(α-bromo-o-tolyl)-3-methoxyacrylate and 0.71 g of 3-hydroxyimino-2-methoxyiminobutyronitrile and the reaction mixture is stirred for one hour. It is then treated with ice-water, the oil which forms crystallizing after a short time. The crystals are filtered off with suction, washed with water and recrystallized from ethyl acetate/hexane. The end product is obtained in the form of pale brown crystals of m.p. 123°–124° C. (Comp. No. 1.1).

Example H-2

Preparation of the compound

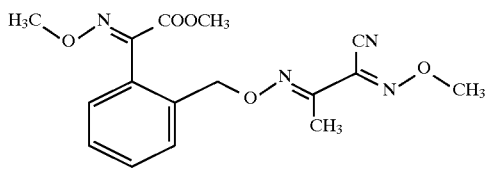

0.42 g of a 60% sodium hydride dispersion is washed with hexane and treated with 10 ml of N,N-dimethylformamide. To this suspension there are added 2.9 g of methyl 2-(2-bromomethylphenyl)glyoxylate O-methyl oxime and 1.4 g of 3-hydroximino-2-methoxyiminobutyronitrile and the reaction mixture is stirred for one hour. It is then treated with ice-water, the oil which forms crystallizing after a short time. The crystals are filtered off with suction and washed with water, then dried and then washed with diethyl ether. The end product is obtained in the form of grey crystals of m.p. 131°–134° C. (Comp. No. 2.1).

Example H-3

Preparation of the compound

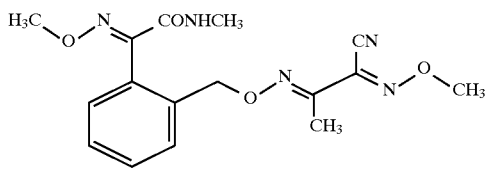

1.04 g of the compound obtained under H-2 are stirred for 2 hours at room temperature in 10 ml of a 33% ethanolic methylamine solution. Ethanol and excess methylamine are distilled off and the residue is washed using diethyl ether. The end product remains in the form of grey crystals of m.p. 159°–162° C. (Comp. No. 3.1).

The following compounds, which are part of the narrower scope of the present invention, can be prepared in such a manner or analogously to one of the methods indicated further above.

[$^1$H NMR: chemical shifts in δ(ppm) in $CDCl_3$.]

TABLE 1

[Structure: methyl (E)-2-methoxyimino-2-[2-(aminoxymethyl)phenyl]acetate core with R2, R3, R4, and oxime linkage]

| Ex. No. | R₂ | R₃ | R₄ | m.p. or ¹H NMR of R₂ |
|---|---|---|---|---|
| 1.1 | CH₃ | CN | CH₃ | 123–124° C. |
| 1.2 | CH₃ | CN | CH₃CH₂ | |
| 1.3 | CH₃ | CN | t-butyl | |
| 1.4 | CH₃ | CN | HC≡CCH₂ | |
| 1.5 | CH₃ | CN | cyclopropyl-CH₂ | |
| 1.6 | CH₃ | CN | H₂C=C(Cl)CH₂ | |
| 1.7 | CH₃ | CN | F₃CCH₂ | |
| 1.8 | CH₃ | CN | FCH₂CH₂ | |
| 1.9 | CH₃ | CN | F₃CCH₂CH₂CH₂ | |
| 1.10 | CH₃ | CN | 2,2-dichlorocyclo-propylmethyl | |
| 1.11 | H | CN | CH₃ | |
| 1.12 | CN | CN | CH₃ | |
| 1.13 | CH₃CH₂ | CN | CH₃ | |
| 1.14 | cyclopropyl | CN | CH₃ | |
| 1.15 | CH₃ | COOCH₃ | CH₃ | 99–100° C. |
| 1.16 | CH₃ | COOCH₃ | CH₃CH₂ | |
| 1.17 | CH₃ | COOCH₃ | t-butyl | |
| 1.18 | CH₃ | COOCH₃ | HC≡CCH₂ | |
| 1.19 | CH₃ | COOCH₃ | cyclopropyl-CH₂ | |
| 1.20 | CH₃ | COOCH₃ | H₂C=C(Cl)CH₂ | |
| 1.21 | CH₃ | COOCH₃ | F₃CCH₂ | |
| 1.22 | CH₃ | COOCH₃ | FCH₂CH₂ | |
| 1.23 | CH₃ | COOCH₃ | F₃CCH₂CH₂CH₂ | |
| 1.24 | CH₃ | COOCH₃ | 2,2-dichloro-cyclopropyl-methyl | |
| 1.25 | CH₃ | COOCH₃ | CH₃OCH₂ | |
| 1.26 | H | COOCH₃ | CH₃ | |
| 1.27 | CN | COOCH₃ | CH₃ | |
| 1.28 | cyclopropyl | COOCH₃ | CH₃ | |
| 1.29 | CH₃ | COOCH₂CH₃ | CH₃ | 94–96° C. |
| 1.30 | CH₃ | COOCH₂CH₂CH₃ | CH₃ | |
| 1.31 | CH₃ | COOCH₂CH₂CH₂CH₃ | CH₃ | 2.02 |
| 1.32 | CH₃ | COOC(CH₃)₃ | CH₃ | 2.00 |
| 1.33 | CH₃ | COOCH(CH₃)₂ | CH₃ | 99–100° C. |
| 1.34 | CH₃ | COOCH₂-cyclopropyl | CH₃ | |
| 1.35 | CH₃ | COOCH₂CH=CH₂ | CH₃ | 81–82° C. |
| 1.36 | CH₃ | COOCH₂C≡CH | CH₃ | |
| 1.37 | CH₃ | COOCH₂CN | CH₃ | |
| 1.38 | CH₃ | COOCH₂CF₃ | CH₃ | |
| 1.39 | CH₃ | COOCH₂CH₂OCH₃ | CH₃ | |
| 1.40 | CH₃ | COOCH₂CH₂SCH₃ | CH₃ | |
| 1.41 | CH₃ | CON(CH₃)₂ | CH₃ | |
| 1.42 | CH₃ | CON(CH₃)CH₂CH₃ | CH₃ | |
| 1.43 | CH₃ | CON(CH₂CH₃)₂ | CH₃ | 109–110° C. |
| 1.44 | CH₃ | CON(CH₃)CH₂CH₂CH₃ | CH₃ | |

TABLE 1-continued

[Structure: methyl (E)-2-[2-(((aminooxy)methyl)phenyl)]-3-methoxyacrylate derivative with =N-O-CH2-Ar-C(=C(OMe))COOMe on one side and C(R2)=N-O-R4 with R3 substituent]

| Ex. No. | R₂ | R₃ | R₄ | m.p. or ¹H NMR of R₂ |
|---|---|---|---|---|
| 1.45 | CH₃ | CON(piperidinyl) | CH₃ | |
| 1.46 | CH₃ | CON(morpholinyl) | CH₃ | |
| 1.47 | CH₃ | CON(pyrrolidinyl) | CH₃ | |
| 1.48 | CH₃ | CON(N-methylpiperazinyl) | CH₃ | |
| 1.49 | CH₃ | CON(azepanyl/homopiperidinyl) 7-membered | CH₃ | |
| 1.50 | CH₃ | CON(2,6-dimethylmorpholinyl) | CH₃ | |
| 1.51 | CH₃ | CON(CH₂CH₂CN)₂ | CH₃ | |
| 1.52 | CH₃ | SOCH₃ | CH₃ | |
| 1.53 | CH₃ | SO₂CH₃ | CH₃ | |
| 1.54 | CH₃ | SOCH(CH₃)₂ | CH₃ | |
| 1.55 | CH₃ | SO₂CH(CH₃)₂ | CH₃ | |
| 1.56 | CH₃ | SOC(CH₃)₃ | CH₃ | |
| 1.57 | CH₃ | SO₂C(CH₃)₃ | CH₃ | |
| 1.58 | CH₃ | SO—C₆H₅ | CH₃ | 109–110° C. |
| 1.59 | CH₃ | SO₂—C₆H₅ | CH₃ | |
| 1.60 | CH₃ | SO₂—C₆H₄—CH₃ (para) | CH₃ | 2.16 |
| 1.61 | CH₃ | SO₂—C₆H₄—F (para) | CH₃ | |

TABLE 1-continued

[Structure: benzene ring with substituents — H₃C-O-CH=C(COOCH₃)- group and -CH₂-O-N=C(R₂)-C(R₃)=N-O-R₄ group]

| Ex. No. | R₂ | R₃ | R₄ | m.p. or ¹H NMR of R₂ |
|---|---|---|---|---|
| 1.62 | CH₃ | –SO₂–(4-Cl-phenyl) | CH₃ | |
| 1.63 | CH₃ | –SO–(4-CH₃-phenyl) | CH₃ | 2.02 |
| 1.64 | CH₃ | –SO₂–(3-OCH₃, 4-NO₂-phenyl) | CH₃ | |
| 1.65 | CH₃ | –SO₂–(2,4-dichlorophenyl) | CH₃ | |
| 1.66 | CH₃ | 2-Δ²-thiazolinyl | CH₃ | 94–96° C. |
| 1.67 | H | 2-Δ²-thiazolinyl | CH₃ | |
| 1.68 | CN | 2-Δ²-thiazolinyl | CH₃ | |
| 1.69 | CH₃CH₂ | 2-Δ²-thiazolinyl | CH₃ | |
| 1.70 | cyclopropyl | 2-Δ²-thiazolinyl | CH₃ | |
| 1.71 | CH₃ | 2-Δ²-thiazolinyl | CH₃CH₂ | |
| 1.72 | CH₃ | 2-Δ²-thiazolinyl | t-butyl | |
| 1.73 | CH₃ | 2-Δ²-thiazolinyl | HC≡CCH₂ | |
| 1.74 | CH₃ | 2-Δ²-thiazolinyl | cyclopropyl-CH₂ | |
| 1.75 | CH₃ | 2-Δ²-thiazolinyl | H₂C=C(Cl)CH₂ | |
| 1.76 | CH₃ | 2-Δ²-thiazolinyl | F₃CCH₂ | |
| 1.77 | CH₃ | 2-Δ²-thiazolinyl | FCH₂CH₂ | |
| 1.78 | CH₃ | 2-Δ²-thiazolinyl | F₃CCH₂CH₂CH₂ | |
| 1.79 | CH₃ | 2-Δ²-thiazolinyl | 2,2-dichlorocyclo-propylmethyl | |
| 1.80 | CH₃ | 2-thiazolinyl-CH(COOCH₂CH₃) | CH₃ | |
| 1.81 | CH₃ | 2-thiazolinyl-C(CH₃)(CH₃)(COOCH₃) | CH₃ | |

TABLE 1-continued

[Structure: H3C-O-CH=C(COOCH3)-phenyl-CH2-O-N=C(R2)-C(R3)=N-O-R4]

| Ex. No. | R₂ | R₃ | R₄ | m.p. or ¹H NMR of R₂ |
|---|---|---|---|---|
| 1.82 | CH₃ | [5,6-dihydro-4H-1,3-thiazin-2-yl] | CH₃ | |
| 1.83 | CH₃ | 2-Δ²-oxazolinyl | CH₃ | |
| 1.84 | CH₃ | 2-Δ²-oxazolinyl | CH₃CH₂ | |
| 1.85 | CH₃ | 2-Δ²-oxazolinyl | t-butyl | |
| 1.86 | CH₃ | 2-Δ²-oxazolinyl | HC≡CCH₂ | |
| 1.87 | CH₃ | 2-Δ²-oxazolinyl | cyclopropyl-CH₂ | |
| 1.88 | CH₃ | 2-Δ²-oxazolinyl | H₂C=C(Cl)CH₂ | |
| 1.89 | CH₃ | 2-Δ²-oxazolinyl | F₃CCH₂ | |
| 1.90 | CH₃ | 2-Δ²-oxazolinyl | FCH₂CH₂ | |
| 1.91 | CH₃ | 2-Δ²-oxazolinyl | F₃CCH₂CH₂CH₂ | |
| 1.92 | CH₃ | 2-Δ²-oxazolinyl | 2,2-dichlorocyclo-propylmethyl | |
| 1.93 | CH₃ | [4-methyl-6,6-dimethyl-5,6-dihydro-4H-1,3-oxazin-2-yl] | CH₃ | |
| 1.94 | CH₃ | [4-methyl-4,5-dihydro-oxazol-2-yl] | CH₃ | |
| 1.95 | CH₃ | [4,4-dimethyl-4,5-dihydro-oxazol-2-yl] | CH₃ | 2.05 |
| 1.96 | CH₃ | 2-thiazolyl | CH₃ | 2.19/2.27 (E/Z) |
| 1.97a | CH₃ | 2-pyridyl | CH₃ | 114–116° C. (isomer 1) |
| 1.97b | CH₃ | 2-pyridyl | CH₃ | oil (isomer 2) |
| 1.98 | CH₃ | 3-pyridyl | CH₃ | oil |
| 1.99 | CH₃ | 4-pyridyl | CH₃ | |
| 1.100 | CH₃ | 2-pyrimidinyl | CH₃ | 139–141° C. |
| 1.101 | CH₃ | 4-chloro-5-cyano-6-methylthio-2-pyrimidinyl | CH₃ | |
| 1.102 | CH₃ | 4,6-dichloro-2-pyrimidinyl | CH₃ | |
| 1.103 | CH₃ | 3-methoxy-2-pyrazinyl | CH₃ | |
| 1.104 | CH₃ | 2-pyrazinyl | CH₃ | oil |
| 1.105 | CH₃ | 5-ethoxycarbonyl-4-trifluoromethyl-2-thiazolyl | CH₃ | |

TABLE 1-continued

[Structure: H₃C-O-CH=C(COOCH₃)-[phenyl]-CH₂-O-N=C(R₂)-C(R₃)=N-O-R₄]

| Ex. No. | R₂ | R₃ | R₄ | m.p. or ¹H NMR of R₂ |
|---|---|---|---|---|
| 1.106 | CH₃ | [2-thiazolyl with CH(CH₃)CH₂-] | CH₃ | |
| 1.107 | CH₃ | COOCH₂—C₆H₅ | CH₃ | 2.02 |
| 1.108 | CH₃ | 2-furyl | CH₃ | oil |
| 1.109 | CH₃ | 5-methyl-3-isoxazolyl | CH₃ | oil |
| 1.110 | CH₃ | 4-methyl-(1,2,3-thiadiazol)-5-yl | CH₃ | 95–97° C. |
| 1.111 | CH₃ | 2-quinoxalinyl | CH₃ | oil |
| 1.112 | CH₃ | 2-benzothiazolyl | CH₃ | oil |
| 1.113 | CH₃ | 4-pyrimidinyl | CH₃ | resin |
| 1.114a | CH₃ | 5-methyl-2-furyl | CH₃ | oil (isomer 1) |
| 1.114b | CH₃ | 5-methyl-2-furyl | CH₃ | oil (isomer 2) |
| 1.115 | CH₃ | 2-benzothienyl | CH₃ | |
| 1.116 | CH₃ | 5-ethyl-2-furyl | CH₃ | oil |
| 1.117 | CH₃ | 1-methyl-2-pyrrolyl | CH₃ | |
| 1.118 | CH₃ | 5-chloro-3-pyridyl | CH₃ | |
| 1.119 | CH₃ | 6-chloro-3-pyridyl | CH₃ | |
| 1.120 | CH₃ | 2-chloro-3-pyridyl | CH₃ | |
| 1.121 | CH₃ | 2,3-dichloro-5-pyridyl | CH₃ | |
| 1.122 | CH₃ | 6-fluoro-3-pyridyl | CH₃ | |
| 1.123 | CH₃ | 6-methyl-3-pyridyl | CH₃ | |
| 1.124 | CH₃ | 6-methoxy-3-pyridyl | CH₃ | |
| 1.125 | CH₃ | 6-methylthio-3-pyridyl | CH₃ | |
| 1.126 | CH₃ | 5-chloro-2-pyrazinyl | CH₃ | |
| 1.127 | CH₃ | 6-chloro-2-quinoxalinyl | CH₃ | |

TABLE 2

[Structure: H₃C-O-N=C(COOCH₃)-[phenyl]-CH₂-O-N=C(R₂)-C(R₃)=N-O-R₄]

| Ex. No. | R₂ | R₃ | R₄ | m.p. or ¹H NMR of R₂ |
|---|---|---|---|---|
| 2.1 | CH₃ | CN | CH₃ | 131–134° C. |
| 2.2 | CH₃ | CN | CH₃CH₂ | |
| 2.3 | CH₃ | CN | t-butyl | |
| 2.4 | CH₃ | CN | HC≡CCH₂ | |
| 2.5 | CH₃ | CN | cyclopropyl-CH₂ | |
| 2.6 | CH₃ | CN | H₂C=C(Cl)CH₂ | |
| 2.7 | CH₃ | CN | F₃CCH₂ | |
| 2.8 | CH₃ | CN | FCH₂CH₂ | |
| 2.9 | CH₃ | CN | F₃CCH₂CH₂ | |
| 2.10 | CH₃ | CN | 2,2-dichlorocyclopropylmethyl | |

TABLE 2-continued

| Ex. No. | R₂ | R₃ | R₄ | m.p. or ¹H NMR of R₂ |
|---|---|---|---|---|
| 2.11 | H | CN | CH₃ | |
| 2.12 | CN | CN | CH₃ | |
| 2.13 | CH₃CH₂ | CN | CH₃ | |
| 2.14 | 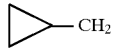 | CN | CH₃ | |
| 2.15 | CH₃ | COOCH₃ | CH₃ | 113–114° C. |
| 2.16 | CH₃ | COOCH₃ | CH₃CH₂ | |
| 2.17 | CH₃ | COOCH₃ | t-butyl | |
| 2.18 | CH₃ | COOCH₃ | HC≡CCH₂ | |
| 2.19 | CH₃ | COOCH₃ | —CH₂ | |
| 2.20 | CH₃ | COOCH₃ | H₂C=C(Cl)CH₂ | |
| 2.21 | CH₃ | COOCH₃ | F₃CCH₂ | |
| 2.22 | CH₃ | COOCH₃ | FCH₂CH₂ | |
| 2.23 | CH₃ | COOCH₃ | F₃CCH₂CH₂CH₂ | |
| 2.24 | CH₃ | COOCH₃ | 2,2-dichlorocyclo-propylmethyl | |
| 2.25 | CH₃ | COOCH₃ | CH₃OCH₂ | |
| 2.26 | H | COOCH₃ | CH₃ | |
| 2.27 | CN | COOCH₃ | CH₃ | |
| 2.28 |  | COOCH₃ | CH₃ | |
| 2.29 | CH₃ | COOCH₂CH₃ | CH₃ | |
| 2.30 | CH₃ | COOCH₂CH₂CH₃ | CH₃ | |
| 2.31 | CH₃ | COOCH₂CH₂CH₂CH₃ | CH₃ | |
| 2.32 | CH₃ | COOC(CH₃)₃ | CH₃ | 82–83° C. |
| 2.33 | CH₃ | COOCH(CH₃)₂ | CH₃ | |
| 2.34 | CH₃ | COOCH₂— | CH₃ | |
| 2.35 | CH₃ | COOCH₂CH=CH₂ | CH₃ | 74–75° C. |
| 2.36 | CH₃ | COOCH₂C≡CH | CH₃ | |
| 2.37 | CH₃ | COOCH₂CN | CH₃ | |
| 2.38 | CH₃ | COOCH₂CF₃ | CH₃ | |
| 2.39 | CH₃ | COOCH₂CH₂OCH₃ | CH₃ | |
| 2.40 | CH₃ | COOCH₂CH₂SCH₃ | CH₃ | |
| 2.41 | CH₃ | CON(CH₃)₂ | CH₃ | |
| 2.42 | CH₃ | CON(CH₃)CH₂CH₃ | CH₃ | |
| 2.43 | CH₃ | CON(CH₂CH₃)₂ | CH₃ | |
| 2.44 | CH₃ | CON(CH₃)CH₂CH₂CH₃ | CH₃ | |
| 2.45 | CH₃ |  | CH₃ | |
| 2.46 | CH₃ |  | CH₃ | |
| 2.47 | CH₃ |  | CH₃ | |

TABLE 2-continued

[Structure: H₃C-O-N=C(COOCH₃)-[benzene ring]-CH₂-O-N=C(R₂)-C(R₃)=N-O-R₄]

| Ex. No. | R₂ | R₃ | R₄ | m.p. or ¹H NMR of R₂ |
|---|---|---|---|---|
| 2.48 | CH₃ | CON(piperazine)N—CH₃ | CH₃ | |
| 2.49 | CH₃ | CON(azocane) | CH₃ | |
| 2.50 | CH₃ | CON(2,6-dimethylmorpholine) | CH₃ | |
| 2.51 | CH₃ | CON(CH₂CH₂CN)₂ | CH₃ | |
| 2.52 | CH₃ | SOCH₃ | CH₃ | |
| 2.53 | CH₃ | SO₂CH₃ | CH₃ | |
| 2.54 | CH₃ | SOCH(CH₃)₂ | CH₃ | |
| 2.55 | CH₃ | SO₂CH(CH₃)₂ | CH₃ | |
| 2.56 | CH₃ | SOC(CH₃)₃ | CH₃ | |
| 2.57 | CH₃ | SO₂C(CH₃)₃ | CH₃ | |
| 2.58 | CH₃ | SO—phenyl | CH₃ | 137–138° C. |
| 2.59 | CH₃ | SO₂—phenyl | CH₃ | |
| 2.60 | CH₃ | SO₂—C₆H₄—CH₃ | CH₃ | |
| 2.61 | CH₃ | SO₂—C₆H₄—F | CH₃ | |
| 2.62 | CH₃ | SO₂—C₆H₄—Cl | CH₃ | |
| 2.63 | CH₃ | SO—C₆H₄—CH₃ | CH₃ | |
| 2.64 | CH₃ | SO₂—C₆H₃(OCH₃)(NO₂) | CH₃ | |

TABLE 2-continued

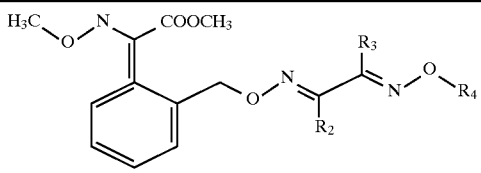

| Ex. No. | R₂ | R₃ | R₄ | m.p. or ¹H NMR of R₂ |
|---|---|---|---|---|
| 2.65 | CH₃ | 3,5-dichlorophenyl-SO₂- | CH₃ | |
| 2.66 | CH₃ | 2-Δ²-thiazolinyl | CH₃ | 97–98° C. |
| 2.67 | H | 2-Δ²-thiazolinyl | CH₃ | |
| 2.68 | CN | 2-Δ²-thiazolinyl | CH₃ | |
| 2.69 | CH₃CH₂ | 2-Δ²-thiazolinyl | CH₃ | |
| 2.70 | cyclopropyl | 2-Δ²-thiazolinyl | CH₃ | |
| 2.71 | CH₃ | 2-Δ²-thiazolinyl | CH₃CH₂ | |
| 2.72 | CH₃ | 2-Δ²-thiazolinyl | t-butyl | |
| 2.73 | CH₃ | 2-Δ²-thiazolinyl | HC≡CCH₂ | |
| 2.74 | CH₃ | 2-Δ²-thiazolinyl | cyclopropyl-CH₂ | |
| 2.75 | CH₃ | 2-Δ²-thiazolinyl | H₂C=C(Cl)CH₂ | |
| 2.76 | CH₃ | 2-Δ²-thiazolinyl | F₃CCH₂ | |
| 2.77 | CH₃ | 2-Δ²-thiazolinyl | FCH₂CH₂ | |
| 2.78 | CH₃ | 2-Δ²-thiazolinyl | F₃CCH₂CH₂CH₂ | |
| 2.79 | CH₃ | 2-Δ²-thiazolinyl | 2,2-dichlorocyclopropylmethyl | |
| 2.80 | CH₃ | 4-(COOCH₂CH₃)-2-Δ²-thiazolinyl | CH₃ | |
| 2.81 | CH₃ | 4,4-dimethyl-5-(COOCH₃)-2-Δ²-thiazolinyl | CH₃ | |
| 2.82 | CH₃ | 2-Δ²-thiazinyl | CH₃ | |
| 2.83 | CH₃ | 2-Δ²-oxazolinyl | CH₃ | |
| 2.84 | CH₃ | 2-Δ²-oxazolinyl | CH₃CH₂ | |
| 2.85 | CH₃ | 2-Δ²-oxazolinyl | t-butyl | |
| 2.86 | CH₃ | 2-Δ²-oxazolinyl | HC≡CCH₂ | |
| 2.87 | CH₃ | 2-Δ²-oxazolinyl | cyclopropyl-CH₂ | |
| 2.88 | CH₃ | 2-Δ²-oxazolinyl | H₂C=C(Cl)CH₂ | |
| 2.89 | CH₃ | 2-Δ²-oxazolinyl | F₃CCH₂ | |
| 2.90 | CH₃ | 2-Δ²-oxazolinyl | FCH₂CH₂ | |
| 2.91 | CH₃ | 2-Δ²-oxazolinyl | F₃CCH₂CH₂CH₂ | |
| 2.92 | CH₃ | 2-Δ²-oxazolinyl | 2,2-dichlorocyclopropylmethyl | |

TABLE 2-continued

[Structure: benzene ring with H3C-O-N=C(COOCH3)- group and -CH2-O-N=C(R2)-C(R3)=N-O-R4 group]

| Ex. No. | R₂ | R₃ | R₄ | m.p. or ¹H NMR of R₂ |
|---|---|---|---|---|
| 2.93 | CH₃ | [structure: oxazoline with CH₃ and C(CH₃)₂ substituents] | CH₃ | |
| 2.94 | CH₃ | [structure: oxazoline with CH₃ substituent] | CH₃ | |
| 2.95 | CH₃ | [structure: oxazoline with C(CH₃)₂ substituent] | CH₃ | 71–74° C. |
| 2.96 | CH₃ | 2-thiazolyl | CH₃ | 2.13/2.22 (E/Z) |
| 2.97 | CH₃ | 2-pyridyl | CH₃ | 113–115° C. |
| 2.98 | CH₃ | 3-pyridyl | CH₃ | oil |
| 2.99 | CH₃ | 4-pyridyl | CH₃ | |
| 2.100 | CH₃ | 2-pyrimidinyl | CH₃ | |
| 2.101 | CH₃ | 4-chloro-5-cyano-6-methylthio-2-pyrimidinyl | CH₃ | |
| 2.102 | CH₃ | 4,6-dichloro-2-pyrimidinyl | CH₃ | |
| 2.103 | CH₃ | 3-methoxy-2-pyrazinyl | CH₃ | |
| 2.104 | CH₃ | 2-pyrazinyl | CH₃ | oil |
| 2.105 | CH₃ | 5-ethoxycarbonyl-4-trifluoromethyl-2-thiazolyl | CH₃ | |
| 2.106 | CH₃ | [structure: thiazoline with CH₃ and ethyl substituents] | CH₃ | |
| 2.107 | CH₃ | COOCH₂—C₆H₅ | CH₃ | 2.00 |
| 2.108a | CH₃ | 2-furyl | CH₃ | oil (isomer 1) |
| 2.108b | CH₃ | 2-furyl | CH₃ | oil (isomer 2) |
| 2.109 | CH₃ | 5-methyl-3-isoxazolyl | CH₃ | 111–113° C. |
| 2.110 | CH₃ | 4-methyl-(1,2,3-thiadiazol)-5-yl | CH₃ | |
| 2.111 | CH₃ | 2-quinoxalinyl | CH₃ | oil |
| 2.112 | CH₃ | 2-benzothiazolyl | CH₃ | 126–127° C. |
| 2.113 | CH₃ | 4-pyrimidinyl | CH₃ | |
| 2.114 | CH₃ | 5-methyl-2-furyl | CH₃ | oil |
| 2.115 | CH₃ | 2-benzothienyl | CH₃ | |
| 2.116 | CH₃ | 5-ethyl-2-furyl | CH₃ | oil |
| 2.117 | CH₃ | 1-methyl-2-pyrrolyl | CH₃ | |
| 2.118 | CH₃ | 5-chloro-3-pyridyl | CH₃ | |
| 2.119 | CH₃ | 6-chloro-3-pyridyl | CH₃ | |
| 2.120 | CH₃ | 2-chloro- | CH₃ | 115° C. |

TABLE 2-continued

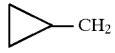

| Ex. No. | R₂ | R₃ | R₄ | m.p. or ¹H NMR of R₂ |
|---|---|---|---|---|
| 2.121 | CH₃ | 3-pyridyl 2,3-dichloro-5-pyridyl | CH₃ | 102–106° C. |
| 2.122 | CH₃ | 6-fluoro-3-pyridyl | CH₃ | |
| 2.123 | CH₃ | 6-methyl-3-pyridyl | CH₃ | |
| 2.124 | CH₃ | 6-methoxy-3-pyridyl | CH₃ | |
| 2.125 | CH₃ | 6-methylthio-3-pyridyl | CH₃ | |
| 2.126 | CH₃ | 5-chloro-2-pyrazinyl | CH₃ | |
| 2.127 | CH₃ | 6-chloro-2-quinoxalinyl | CH₃ | |

TABLE 3

| Ex. No. | R₂ | R₃ | R₄ | m.p. or ¹H NMR of R₂ |
|---|---|---|---|---|
| 3.1 | CH₃ | CN | CH₃ | 159–162° C. |
| 3.2 | CH₃ | CN | CH₃CH₂ | |
| 3.3 | CH₃ | CN | t-butyl | |
| 3.4 | CH₃ | CN | HC≡CCH₂ | |
| 3.5 | CH₃ | CN | cyclopropyl-CH₂ | |
| 3.6 | CH₃ | CN | H₂C=C(Cl)CH₂ | |
| 3.7 | CH₃ | CN | F₃CCH₂ | |
| 3.8 | CH₃ | CN | FCH₂CH₂ | |
| 3.9 | CH₃ | CN | F₃CCH₂CH₂CH₂ | |
| 3.10 | CH₃ | CN | 2,2-dichlorocyclo-propylmethyl | |
| 3.11 | H | CN | CH₃ | |
| 3.12 | CN | CN | CH₃ | |
| 3.13 | CH₃CH₂ | CN | CH₃ | |
| 3.14 | cyclopropyl | CN | CH₃ | |
| 3.15 | CH₃ | COOCH₃ | CH₃ | 1.98 |
| 3.16 | CH₃ | COOCH₃ | CH₃CH₂ | |
| 3.17 | CH₃ | COOCH₃ | t-butyl | |
| 3.18 | CH₃ | COOCH₃ | HC≡CCH₂ | |
| 3.19 | CH₃ | COOCH₃ | cyclopropyl-CH₂ | |
| 3.20 | CH₃ | COOCH₃ | H₂C=C(Cl)CH₂ | |
| 3.21 | CH₃ | COOCH₃ | F₃CCH₂ | |
| 3.22 | CH₃ | COOCH₃ | FCH₂CH₂ | |
| 3.23 | CH₃ | COOCH₃ | F₃CCH₂CH₂CH₂ | |
| 3.24 | CH₃ | COOCH₃ | 2,2-dichlorocyclo-propylmethyl | |

TABLE 3-continued

| Ex. No. | R₂ | R₃ | R₄ | m.p. or ¹H NMR of R₂ |
|---|---|---|---|---|
| 3.25 | CH₃ | COOCH₃ | CH₂OCH₂ | |
| 3.26 | H | COOCH₃ | CH₃ | |
| 3.27 | CN | COOCH₃ | CH₃ | |
| 3.28 |  | COOCH₃ | CH₃ | |
| 3.29 | CH₃ | COOCH₂CH₃ | CH₃ | |
| 3.30 | CH₃ | COOCH₂CH₂CH₃ | CH₃ | |
| 3.31 | CH₃ | COOCH₂CH₂CH₂CH₃ | CH₃ | 127–128° C. |
| 3.32 | CH₃ | COOC(CH₃)₃ | CH₃ | |
| 3.33 | CH₃ | COOCH(CH₃)₂ | CH₃ | |
| 3.34 | CH₃ |  | CH₃ | |
| 3.35 | CH₃ | COOCH₂CH=CH₂ | CH₃ | 1.98 |
| 3.36 | CH₃ | COOCH₂C≡CH | CH₃ | |
| 3.37 | CH₃ | COOCH₂CN | CH₃ | |
| 3.38 | CH₃ | COOCH₂CF₃ | CH₃ | 1.90 |
| 3.39 | CH₃ | COOCH₂CH₂OCH₃ | CH₃ | |
| 3.40 | CH₃ | COOCH₂CH₂SCH₃ | CH₃ | |
| 3.41 | CH₃ | CON(CH₃)₂ | CH₃ | |
| 3.42 | CH₃ | CON(CH₃)CH₂CH₃ | CH₃ | |
| 3.43 | CH₃ | CON(CH₂CH₃)₂ | CH₃ | |
| 3.44 | CH₃ | CON(CH₃)CH₂CH₂CH₃ | CH₃ | |
| 3.45 | CH₃ | 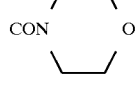 | CH₃ | |
| 3.46 | CH₃ | 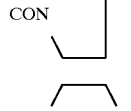 | CH₃ | |
| 3.47 | CH₃ | 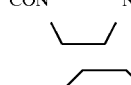 | CH₃ | |
| 3.48 | CH₃ | 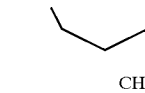 | CH₃ | |
| 3.49 | CH₃ | 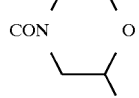 | CH₃ | |
| 3.50 | CH₃ |  | CH₃ | |
| 3.51 | CH₃ | CON(CH₂CH₂CN)₂ | CH₃ | |
| 3.52 | CH₃ | SOCH₃ | CH₃ | |
| 3.53 | CH₃ | SO₂CH₃ | CH₃ | |

TABLE 3-continued

[Structure: benzene ring with ortho substituents: -C(=NOCH₃)CONHCH₃ and -CH₂-O-N=C(R₂)-C(R₃)=N-O-R₄]

| Ex. No. | R₂ | R₃ | R₄ | m.p. or ¹H NMR of R₂ |
|---|---|---|---|---|
| 3.54 | CH₃ | SOCH(CH₃)₂ | CH₃ | |
| 3.55 | CH₃ | SO₂CH(CH₃)₂ | CH₃ | |
| 3.56 | CH₃ | SOC(CH₃)₃ | CH₃ | |
| 3.57 | CH₃ | SO₂C(CH₃)₃ | CH₃ | |
| 3.58 | CH₃ | SO-phenyl | CH₃ | |
| 3.59 | CH₃ | SO₂-phenyl | CH₃ | |
| 3.60 | CH₃ | SO₂-(4-CH₃-phenyl) | CH₃ | |
| 3.61 | CH₃ | SO₂-(4-F-phenyl) | CH₃ | |
| 3.62 | CH₃ | SO₂-(4-Cl-phenyl) | CH₃ | |
| 3.63 | CH₃ | SO-(4-CH₃-phenyl) | CH₃ | |
| 3.64 | CH₃ | SO₂-(3-OCH₃-2-NO₂-phenyl) | CH₃ | |
| 3.65 | CH₃ | SO₂-(2,4-dichlorophenyl) | CH₃ | |
| 3.66 | CH₃ | 2-Δ²-thiazolinyl | CH₃ | 154–155° C. |
| 3.67 | H | 2-Δ²-thiazolinyl | CH₃ | |
| 3.68 | CN | 2-Δ²-thiazolinyl | CH₃ | |
| 3.69 | CH₃CH₂ | 2-Δ²-thiazolinyl | CH₃ | |
| 3.70 | cyclopropyl | 2-Δ²-thiazolinyl | CH₃ | |
| 3.71 | CH₃ | 2-Δ²-thiazolinyl | CH₃CH₂ | |
| 3.72 | CH₃ | 2-Δ²-thiazolinyl | t-butyl | |
| 3.73 | CH₃ | 2-Δ²-thiazolinyl | HC≡CCH₂ | |

TABLE 3-continued

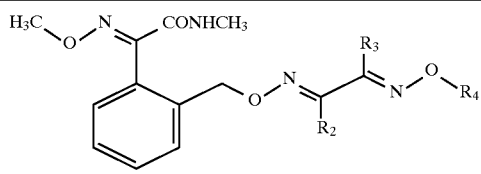

| Ex. No. | R$_2$ | R$_3$ | R$_4$ | m.p. or $^1$H NMR of R$_2$ |
|---|---|---|---|---|
| 3.74 | CH$_3$ | 2-Δ$^2$-thiazolinyl | cyclopropyl-CH$_2$ | |
| 3.75 | CH$_3$ | 2-Δ$^2$-thiazolinyl | H$_2$C=C(Cl)CH$_2$ | |
| 3.76 | CH$_3$ | 2-Δ$^2$-thiazolinyl | F$_3$CCH$_2$ | |
| 3.77 | CH$_3$ | 2-Δ$^2$-thiazolinyl | FCH$_2$CH$_2$ | |
| 3.78 | CH$_3$ | 2-Δ$^2$-thiazolinyl | F$_3$CCH$_2$CH$_2$ | |
| 3.79 | CH$_3$ | 2-Δ$^2$-thiazolinyl | 2,2-dichlorocyclo-propylmethyl | |
| 3.80 | CH$_3$ | thiazolinyl-COOCH$_2$CH$_3$ | CH$_3$ | |
| 3.81 | CH$_3$ | dimethyl-thiazolinyl-COOCH$_3$ | CH$_3$ | |
| 3.82 | CH$_3$ | thiazinyl | CH$_3$ | |
| 3.83 | CH$_3$ | 2-Δ$^2$-oxazolinyl | CH$_3$ | |
| 3.84 | CH$_3$ | 2-Δ$^2$-oxazolinyl | CH$_3$CH$_2$ | |
| 3.85 | CH$_3$ | 2-Δ$^2$-oxazolinyl | t-butyl | |
| 3.86 | CH$_3$ | 2-Δ$^2$-oxazolinyl | HC≡CCH$_2$ | |
| 3.87 | CH$_3$ | 2-Δ$^2$-oxazolinyl | cyclopropyl-CH$_2$ | |
| 3.88 | CH$_3$ | 2-Δ$^2$-oxazolinyl | H$_2$C=C(Cl)CH$_2$ | |
| 3.89 | CH$_3$ | 2-Δ$^2$-oxazolinyl | F$_3$CCH$_2$ | |
| 3.90 | CH$_3$ | 2-Δ$^2$-oxazolinyl | FCH$_2$CH$_2$ | |
| 3.91 | CH$_3$ | 2-Δ$^2$-oxazolinyl | F$_3$CCH$_2$CH$_2$ | |
| 3.92 | CH$_3$ | 2-Δ$^2$-oxazolinyl | 2,2-dichlorocyclo-propylmethyl | |
| 3.93 | CH$_3$ | oxazinyl (substituted) | CH$_3$ | |
| 3.94 | CH$_3$ | methyl-oxazinyl | CH$_3$ | |

TABLE 3-continued

Structure: 2-[H3C-O-N=C(CONHCH3)]-phenyl-CH2-O-N=C(R2)-C(R3)=N-O-R4

| Ex. No. | R2 | R3 | R4 | m.p. or $^1$H NMR of R2 |
|---|---|---|---|---|
| 3.95 | CH3 | (isoxazoline: O-N-C(CH3)2 ring) | CH3 | |
| 3.96 | CH3 | 2-thiazolyl | CH3 | 2.09/2.19 (E/Z) |
| 3.97 | CH3 | 2-pyridyl | CH3 | 182–184° C. |
| 3.98 | CH3 | 3-pyridyl | CH3 | resin |
| 3.99 | CH3 | 4-pyridyl | CH3 | |
| 3.100 | CH3 | 2-pyrimidinyl | CH3 | |
| 3.101 | CH3 | 4-chloro-5-cyano-6-methylthio-2-pyrimidinyl | CH3 | |
| 3.102 | CH3 | 4,6-dichloro-2-pyrimidinyl | CH3 | |
| 3.103 | CH3 | 3-methoxy-2-pyrazinyl | CH3 | |
| 3.104 | CH3 | 2-pyrazinyl | CH3 | oil |
| 3.105 | CH3 | 5-ethoxycarbonyl-4-trifluoromethyl-2-thiazolyl | CH3 | |
| 3.106 | CH3 | (thiazoline: S-N-C(CH3)-CH3 ring) | CH3 | |
| 3.107 | CH3 | COOCH2—C6H5 | CH3 | 1.98 |
| 3.108 | CH3 | 2-furyl | CH3 | resin |
| 3.109 | CH3 | 5-methyl-3-isoxazolyl | CH3 | 131–133° C. |
| 3.110 | CH3 | 4-methyl-(1,2,3-thiadiazol)-5-yl | CH3 | |
| 3.111 | CH3 | 2-quinoxalinyl | CH3 | oil |
| 3.112 | CH3 | 2-benzothiazolyl | CH3 | 162–164° C. |
| 3.113 | CH3 | 4-pyrimidinyl | CH3 | |
| 3.114 | CH3 | 5-methyl-2-furyl | CH3 | resin |
| 3.115 | CH3 | 2-benzothienyl | CH3 | |
| 3.116 | CH3 | 5-ethyl-2-furyl | CH3 | 141–143° C. |
| 3.117 | CH3 | 1-methyl-2-pyrrolyl | CH3 | |
| 3.118 | CH3 | 5-chloro-3-pyridyl | CH3 | |
| 3.119 | CH3 | 6-chloro-3-pyridyl | CH3 | |
| 3.120 | CH3 | 2-chloro-3-pyridyl | CH3 | |
| 3.121 | CH3 | 2,3-dichloro-5-pyridyl | CH3 | 125–128° C. |
| 3.122 | CH3 | 6-fluoro-3-pyridyl | CH3 | |
| 3.123 | CH3 | 6-methyl-3-pyridyl | CH3 | |
| 3.124 | CH3 | 6-methoxy-3-pyridyl | CH3 | |
| 3.125 | CH3 | 6-methylthio-3-pyridyl | CH3 | |
| 3.126 | CH3 | 5-chloro-2-pyrazinyl | CH3 | |
| 3.127 | CH3 | 6-chloro-2-quinoxalinyl | CH3 | |

TABLE 4

![Structure]

| Ex. No. | X | Y | R₁ | R₃ | m.p. or ¹H NMR of *CH₃ |
|---|---|---|---|---|---|
| 4.1 | CH | O | CH₂CH₃ | CN | |
| 4.2 | CH | O | CH₂CH₃ | COOCH₃ | |
| 4.3 | CH | O | CH₂CH₃ | 2-Δ²-thiazolinyl | |
| 4.4 | N | O | CH₂CH₃ | CN | |
| 4.5 | N | O | CH₂CH₃ | COOCH₃ | |
| 4.6 | N | O | CH₂CH₃ | 2-Δ²-thiazolinyl | |
| 4.7 | N | NH | CH₂CH₃ | CN | |
| 4.8 | N | NH | CH₂CH₃ | COOCH₃ | |
| 4.9 | N | NH | CH₂CH₃ | 2-Δ²-thiazolinyl | |
| 4.10 | CH | O | CH(CH₃)₂ | CN | |
| 4.11 | CH | O | CH₂CH₂CH₂CH₃ | CN | |

PREPARATION OF INTERMEDIATES

Example H-4

Preparation of

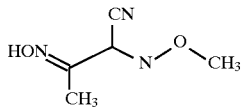

1.7 g of a 60% sodium hydride dispersion is washed with hexane and treated with 40 ml of N,N-dimethylformamide. To this suspension there is added, with ice-cooling, 4.5 g of 2-hydroxyimino-3-oxobutyronitrile, a little at a time. Half an hour after the evolution of hydrogen has ceased, 2.75 ml of methyl iodide is added dropwise. After the mixture has been stirred for 3 hours at room temperture, it is poured into ice-water and extracted 3× using 20 ml of diethyl ether in each case. After drying over sodium sulfate and evaporating the solvent, the brown oil which remains is purified on silica gel by means of ethyl acetate/hexane (1:2).

4.1 g of the yellow oil obtained above together with 3.5 g of hydroxylamine hydrochloride in 20 ml of pyridine are stirred at room temperature for 3 hours. The reaction mixture is poured into ice-water, and the crystals which form after a short time are filtered off. After washing with water and drying, the end product is obtained as pale brown crystals of m.p. 140°–145° C.

The following characteristic representatives of intermediates can be prepared analogously:

TABLE 5

![Structure: HO-N=C(R₂)-C(R₃)=N-O-R₄]

| R₂ | R₃ | R₄ | Physical data |
|---|---|---|---|
| CH₃ | CN | CH₃ | m.p. 140–145° C. |
| CH₃ | COOCH₃ | CH₃ | 77–80° C. |
| CH₃ | COO(CH₂)₃CH₃ | CH₃ | colourless oil |
| CH₃ | COOC(CH₃)₃ | CH₃ | m.p. 111–119° C. |
| CH₃ | CON(CH₂CH₃)₂ | CH₃ | m.p. 115–116° C. |
| CH₃ | CON(morpholino) | CH₃ | |
| CH₃ | CON(piperidino) | CH₃ | |
| CH₃ | 2-Δ²-thiazolinyl | CH₃ | m.p. 162–164° C. |
| CH₃ | 2-Δ²-thiazolinyl | CH₃ | |
| CH₃ | 2,2-dimethyl-oxazoline | CH₃ | white crystals |
| CH₃ | COOCH₂—C₆H₅ | CH₃ | m.p. 59–60° C. |
| CH₃ | COOCH₂CH=CH₂ | CH₃ | pale yellow oil |
| CH₃ | COOCH₂CH₃ | CH₃ | pale yellow oil |
| CH₃ | COOCH(CH₃)₂ | CH₃ | pale yellow oil |
| CH₃ | 2-thiazolyl | CH₃ | oil |
| CH₃ | 2-pyridyl | CH₃ | m.p. 207–210° C. |
| CH₃ | 2-furyl | CH₃ | oil |
| CH₃ | 5-methyl-3-isoxazolyl | CH₃ | oil |
| CH₃ | 4-methyl-(1,2,3-thiadiazol)-5-yl | CH₃ | m.p. 122–124° C. |
| CH₃ | 2-quinoxalinyl | CH₃ | oil |
| CH₃ | 2-pyrazinyl | CH₃ | oil |
| CH₃ | 2-benzothiazolyl | CH₃ | oil |
| CH₃ | 3-pyridyl | CH₃ | |
| CH₃ | 4-pyrimidinyl | CH₃ | |
| CH₃ | 5-methyl-2-furyl | CH₃ | oil |
| CH₃ | 2-benzothienyl | CH₃ | |
| CH₃ | 5-ethyl-2-furyl | CH₃ | oil |
| CH₃ | 1-methyl-2-pyrrolyl | CH₃ | |
| CH₃ | COOCH₂CH₂—OCH₃ | CH₃ | pale yellow oil |

2. Formulation examples of active ingredients of the formula I (%=per cent by weight)

| 2.1. Wettable powders | a) | b) | c) |
|---|---|---|---|
| Active ingredient of Tables 1–4 | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenol polyethylene glycol ether (7–8 mol of ethylene oxide) | — | 2% | — |
| Highly disperse silica | 5% | 10% | 10% |
| Kaolin | 62% | 27% | — |

The active ingredient is mixed thoroughly with the additives and the mixture is ground thoroughly in a suitable mill. This gives wettable powders which can be diluted with water to give suspensions of any desired concentration.

| 2.2. Emulsion concentrate | |
|---|---|
| Active ingredient of Tables 1–4 | 10% |
| Octylphenol polyethylene glycol ether (4–5 mol of ethylene oxide) | 3% |
| Calcium dodecylbenzenesulfonate | 3% |
| Cyclohexanone | 34% |
| Xylene mixture | 50% |

Emulsions of any desired dilution can be prepared from this concentrate by diluting it with water.

| 2.3. Dusts | a) | b) |
|---|---|---|
| Active ingredient of Tables 1–4 | 5% | 8% |
| Talc | 95% | — |
| Kaolin | — | 92% |

Ready-to-use dusts are obtained by mixing the active ingredient with the carrier and grinding the mixture in a suitable mill.

| 2.4. Extruder granules | |
|---|---|
| Active ingredient of Tables 1–4 | 10% |
| Sodium lignosulfonate | 2% |
| Carboxymethylcellulose | 1% |
| Kaolin | 87% |

The active ingredient is mixed with the additives, and the mixture is ground and moistened with water. This mixture is extruded and subsequently dried in a stream of air.

| 2.5. Coated granules | |
|---|---|
| Active ingredient of Tables 1–4 | 3% |
| Polyethylene glycol (MW 200) | 3% |
| Kaolin | 94% |

(MW = molecular weight)

In a mixer, the finely ground active ingredient is applied uniformly to the kaolin which has been moistened with polyethylene glycol. This gives dust-free coated granules.

| 2.6. Suspension concentrate | |
|---|---|
| Active ingredient of Tables 1–4 | 40% |
| Ethylene glycol | 10% |
| Nonylphenol polyethylene glycol ether (15 mol of ethylene oxide) | 6% |
| Sodium lignosulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. This gives a suspension concentrate from which suspensions of any desired dilution can be prepared by diluting it with water.

3. BIOLOGICAL EXAMPLES

A) Microbicidal action

Example B-1

Action against *Phytophthora infestans* on tomatoes
a) Curative action

Tomato plants cv. "Roter Gnom" are grown for three weeks and then sprayed with a zoospore suspension of the fungus and incubated in a cabinet at 18°–20° and saturated atmospheric humidity. The humidification is interrupted after 24 hours. After the plants have dried, they are sprayed with a mixture comprising the active ingredient, formulated as a wettable powder, at a concentration of 200 ppm. After the spray coating has dried on, the plants are returned to the humid chamber for 4 days. Number and size of the characteristic lesions which have appeared after this time are used to assess the efficacy of the test substances.

b) Preventive-systemic action

The active ingredient, formulated as a wettable powder, is applied at a concentration of 60 ppm (relative to the soil volume) to the soil surface of three-week-old tomato plants cv. "Roter Gnom" in pots. After a period of three days has elapsed, the underside of the plants' leaves is sprayed with a zoospore suspension of *Phytophthora infestans*. They are then kept in a spraying cabinet at 18° to 20° C. and saturated atmospheric humidity for 5 days. After this time, characteristic lesions form, whose number and size are used for assessing the efficacy of the test substances. While untreated, but infected, control plants show a disease level of 100%, the active ingredients of the formula I in accordance with one of the Tables 1 to 4, in particular the compounds No. 1.1, 1.15, 1.31, 1.32, 1.66, 1.96, 2.1, 2.15, 2.32, 2.66, 2.96, 3.1, 3.15, 3.32, 3.66, 3.96 and 4.10, allow the disease level to be reduced to 10% or less in both tests.

Example B-2

Action against *Plasmopara viticola* (Bert. et Curt.) (Berl. et DeToni) on grapevines
a) Residual-preventive action Grapevine seedlings cv. "Chasselas" are grown in the greenhouse. When they have reached the 10-leaf stage, 3 plants are sprayed with a mixture (200 ppm of active ingredient). After the spray coating has dried on, the underside of the plants' leaves are infected uniformly with the spore suspension of the fungus. The plants are subsequently kept in a humid chamber for 8 days. After this time, pronounced disease symptoms can be seen on the control plants. Number and size of the lesions on the treated plants are used for assessing the efficacy of the test substances.

b) Curative action

Grapevine seedlings cv. "Chasselas" are grown in the greenhouse and, in the 10-leaf stage, infected on the underside of the leaves with a spore suspension of *Plasmopara viticola* After the plants have remained in a humid chamber for 24 hours, they are sprayed with a mixture of active ingredient (200 ppm of active ingredient). The plants subsequently remain the humid chamber for 7 days. After this time, the disease symptoms can be observed on the control plants. Number and size of the lesions on the treated plants are used for assessing the efficacy of the test substances. In comparison with the control plants, the plants which have been treated with active ingredients of the formula I shows a disease level of 20% or less. The preparations mentioned in test B-1 reduce the disease level to 10–0%.

Example B-3

Action against *Pythium debaryanum* on sugar beet (*Beta vulgaris*)
a) Action of the soil drench The fungus is grown on sterile oat kernels and admixed to a mixture of soil and sand. The soil, which has thus been infected, is filled into flowerpots, and sugar beet seeds are sown in. Immediately after sowing, the test preparations, which are formulated as a wettable powder, are used to drench the soil in the form of an aqueous suspension (20 ppm of active ingredient based on the soil volume). The pots are then placed in the greenhouse at 20°–24° C. for 2–3 weeks. The soil is constantly kept uniformly moist by lightly spraying with water. To evaluate the tests, the emergence of the sugar beet plants and the proportion of healthy and diseased plants is determined.

b) Action after application by seed dressing

The fungus is grown on sterile oat kernels and admixed to a mixture of soil and sand. The soil, which has thus been infected, is filled into flowerpots, and sugar beet seeds are sown in which have been treated with the test preparations which were formulated as a powder for seed treatment (1,000 ppm of active ingredient based on the weight of the seeds). The pots together with the seed were placed in the greenhouse at 20°–24° C. for 2–3 weeks. The soil is constantly kept uniformly moist by lightly spraying with water. To evaluate the tests, the emergence of the sugar beet plants and the proportion of healthy and diseased plants is determined. After treatment with active ingredients of the formula I, over 80% of the plants emerge and have a healthy appearance. Only a few plants of weak appearance are observed in the control pots.

Example B-4

Residual-Protective action against *Cercospora arachidicola* on groundnuts

Groundnut plants 10 to 15 cm in height are sprayed to drip point with an aqueous spray mixture (0.02% of active ingredient) and, 48 hours later, infected with a conidia suspension of the fungus. The plants are incubated at 21° and high atmospheric humidity for 72 hours and subsequently placed in the greenhouse until the characteristic lesions on the leaves have appeared. The action of the active ingredient is assessed 12 days after infection on the basis of number and size of the lesions. Active ingredients of the formula I reduce the lesions to below approximately 10% of the leaf area. In some cases, the disease is controlled completely (disease level 0–5%), for example in the case of treatment with the compounds No. 1.15, 1.66 and 3.15.

Example B-5

Action against *Puccinia graminis* on wheat
a) Residual-protective action 6 days after sowing, wheat plants are sprayed to drip point with an aqueous spray mixture (0.02% of active ingredient) and, 24 hours later, infected with a uredospore suspension of the fungus. After an incubation time of 48 hours (conditions: 95 to 100% relative atmospheric humidity at 20°), the plants are placed in a greenhouse at 22°. The rust pustule development is assessed 12 days after infection.

b) Systemic action

An aqueous spray mixture (0.006% of active ingredient based on the soil volume) is poured next to wheat plants 5 days after sowing. Care is taken that the spray mixture does not come into contact with aerial parts of the plants. 48 hours later, the plants are infected with a uredospore suspension of the fungus. After an incubation time of 48 hours (conditions: 95 to 100% relative atmospheric humidity at 20°), the plants are placed in a greenhouse at 22°. The rust pustule development is assessed 12 days after infection. Compounds of the formula I, for example No. 1.1, 1.15, 1.31, 1.58, 1.60, 1.63, 1.66, 1.96, 1.100, 2.1, 2.58, 2.120, 2.121 3.1, 3.39 3.121 and others, cause a marked reduction in fungus infestation, in some cases down to 10–0%.

Example B-6

Action against *Pyricularia oryzae* on rice
a) Residual-protective action

Rice plants are grown for two weeks and then sprayed to drip point with an aqueous spray mixture (0.02% active ingredient) and, 48 hours later, infected with a conidia suspension of the fungus. Fungus infestation is assessed 5 days after infection, during which a relative atmospheric humidity of 95 to 100% and a temperature of 22° are maintained.

b) Systemic action

An aqueous spray mixture (0.006% of active ingredient based on the soil volume) is poured next to 2-week-old rice plants. Care is taken that the spray mixture does not come into contact with aerial parts of the plants. The pots are then filled with water so that the stem bases of the rice plants are submerged. After 96 hours, the plants are infected with a conidia suspension of the fungus and kept for 5 days at a relative atmospheric humidity of 95 to 100% and a temperature of 24°. Compounds of the formula I prevent to a large extent eruption of the disease on the infected plants.

Example B-7

Residual-protective action against *Venturia inaequalis* on apples

Apple cuttings which have fresh shoots 10 to 20 cm in length are sprayed to drip point with a spray mixture (0.02% of active ingredient) and, 24 hours later, infected with a conidia suspension of the fungus. The plants are incubated at a relative atmospheric humidity of 90 to 100 per cent for 5 days and placed in a greenhouse at 20° to 24° for a further 10 days. Scab attack is assessed 15 days after infection. Most of the compounds of the formula I of one of Tables 1 to 4 have a sustained action against scab diseases.

Example B-8

Action against *Erysiphe graminis* on barley
a) Residual-protective action

Barley plants approximately 8 cm high are sprayed to drip point with an aqueous spray mixture (0.02% of active ingredient) and, 3 to 4 hours later, dusted with conidia of the fungus. The infected plants are placed in a greenhouse at 22°. Fungus infestation is assessed 10 days after infection.

b) Systemic action

An aqueous spray mixture (0.002% of active ingredient based on the soil volume) is poured next to barley plants approximately 8 cm in height. Care is taken that the spray mixture does not come into contact with aerial parts of the plants. 48 hours later, the plants are dusted with conidia of the fungus. The infected plants are placed in a greenhouse at 22°. Fungus infestation is assessed 10 days after infection. Compounds of the formula I, in particular compounds No. 1.1, 1.4, 1.5, 1.14, 1.15, 1.19, 1.25, 1.27, 1.28, 1.31, 1.32, 1.53, 1.58, 1.60, 1.63, 1.66, 1.68, 1.70, 1.76, 1.79, 1.83, 1.96, 1.98, 1.100, 2.1, 2.3, 2.15, 2.32, 2.37, 2.45, 2.58, 2.66, 2.95, 2.100, 2.120, 2.121, 3.1, 3.15, 3.27, 3.39, 3.66, 3.121, 4.1, 4.10 and others, are generally capable of reducing the disease level to less than 20%, in some cases even completely.

Example B-9

Action against *Podosphaera leucotricha* on apple shoots
Residual-protective action Apple cuttings which have fresh shoots of approximately 15 cm are sprayed with a spray mixture (0.06% of active ingredient). After 24 hours, the treated plants are infected with a conidia suspension of the fungus and placed in a controlled-environment cabinet at a relative atmospheric humidity of 70% and at 20°. Fungus infestation is assessed 12 days after infection. The active ingredients of the formula I reduce the disease level to less than 20%. 100% of the control plants are diseased.

Example B-10

Action against *Botrytis cinerea* on apple fruits. Residual-protective action

Artificially damaged apples are treated by dropwise application of a spray mixture (0.02% of active ingredient) to the damaged sites. The treated fruits are subsequently inoculated with a spore suspension of the fungus and incubated at high atmospheric humidity and approximately 20° C. for one week. The fungicidal action of the test substance is deduced from the number of damaged sites which were affected by rot. Active ingredients of the formula I of Tables 1 to 4 are capable of preventing the rot from spreading, in some cases completely.

Example B-11

Action against *Helminthosporium gramineum*

Wheat kernels are contaminated with a spore suspension of the fungus and allowed to dry.

The contaminated kernels are treated with a suspension of the test substance (600 ppm of active ingredient based on the weight of the seeds). After two days, the kernels are placed on suitable agar dishes, and after a further four days, the development of fungal colonies around the kernels is assessed. Number and size of the fungal colonies are used for assessing the test substance. In some cases, compounds of the formula I have a good action, i.e. inhibit fungal colonies.

Example B-12

Action against *Colletotrichum lagenarium* on cucumbers

Cucumber plants are grown for 2 weeks and then sprayed with a spray mixture (concentration 0.002%). After 2 days, the plants are infected with a spore suspension of the fungus ($1.5 \times 10^5$ spores/ml) and incubated at 23° C. and high atmospheric humidity for 36 hours. Incubation is then continued at normal atmospheric humidity and approximately 22°–23° C. The fungus infestation which occurs is assessed 8 days after infection. Untreated, but infected, control plants have a fungus infestation of 100%. Some of the compounds of the formula I cause virtually complete inhibition of the disease.

Example B-13

Action against *Fusarium nivale* on rye

Using a mixing roller, rye cv. Tetrahell which has been infected naturally with *Fusarium nivale* is treated with the test fungicide, the following concentrations being used: 20 or 6 ppm of a.i. (based on the weight of the seeds).

In October, the infected and treated rye is sown in the open in plots of 3 m length and 6 rows, using a drilling machine. 3 replications per concentration.

Until the disease level is assessed, the test plants are grown under normal field conditions (preferably in a region with uninterrupted snow cover during the winter months).

To assess the phytotoxicity, emergence of the seed is scored in autumn and plant density/tillering in spring.

To determine the efficacy of the active ingredient, the percentage of plants infected with Fusarium is counted in the spring immediately after the snow has melted. Treatment with a compound of the formula I resulted in a percentage of diseased plants of less than 5. The emerged plants had a healthy appearance.

Example B-14

Action against *Septoria nodorum* on wheat

Wheat plants in the 3-leaf stage are sprayed with a spray mixture (60 ppm of a.i.) prepared from a wettable powder of the active ingredients.

After 24 hours, the treated plants are infected with a conidia suspension of the fungus. The plants are subsequently incubated at a relative atmospheric humidity of 90–100% for 2 days and then placed in a greenhouse at 20°–24° C. for a further 10 days. 13 days after infection, fungus infestation is assessed. Less than 1% of the wheat plants were diseased.

Example B-15

Action against *Rhizoctonia solani* on rice Protective local soil drench

In a flower dish, a suspension prepared with the formulated test substance (spray mixture) is poured next to 10-day-old rice plants without contaminating aerial parts of the plants. Infection is effected three days later by placing a stem of barley straw which is infected with *Rhizoctonia solani* between the rice plants of each pot. Fungus infestation is assessed after incubation for 6 days in a controlled-environment cabinet at a daytime temperature of 29° C. and a nighttime temperature of 26° C., and a relative atmospheric humidity of 95%. Less than 5% of the rice plants were diseased. The plants had a healthy appearance.

Protective local foliar application 12-day-old rice plants are sprayed with a suspension prepared with formulated test substances. Infection is effected one day later by placing a stem of barley straw which is infected with *Rhizoctonia solani* between the rice plants of each pot. Scoring is effected after incubation for 6 days in a controlled-environment cabinet at a daytime temperature of 29° C. and a nighttime temperature of 26° C., and a relative atmospheric humidity of 95%. Untreated, but infected, control plants show a fungus infestation of 100%. Compounds of the formula I cause, in some cases, complete inhibition of the disease.

B. Insecticidal action

Example B-16

Action against *Aphis craccivora*

Pea seedlings are infected with *Aphis craccivora*, subsequently sprayed with a spray mixture comprising 400 ppm of active ingredient, and then incubated at 20°. By comparing the number of dead aphids on the treated and untreated plants, the percentage reduction in population (% action) is determined after 3 and 6 days. In this test, compounds of Tables 14 have a good action, i.e. a destruction rate of over 80%.

Example B-17

Action against *Diabrotica balteata*

Maize seedlings are sprayed with an aqueous emulsion spray mixture comprising 400 ppm of active ingredient, then, after the spray coating has dried on, populated with 10 second instar larvae of *Diabrotica balteata,* and then placed in a plastic container. The percentage reduction in population (% action) is determined 6 days later by comparing the number of dead larvae between the treated and untreated plants. In this test, compounds of Tables 1–4 have good action.

Example B-18

Action against *Heliothis virescens*

Young soya bean plants are sprayed with an aqueous emulsion spray mixture comprising 400 ppm of active ingredient, then, after the spray coating has dried on, populated with 10 first instar caterpillars of *Heliothis virescens,* and then placed in a plastic container. The percentage reduction in population and in feeding damage (% action) is determined 6 days later by comparing the number of dead caterpillars and the feeding damage between the treated and untreated plants. In this test, compounds of Tables 1–4 have good action. Compound No. 1.40, in particular, has a potent insecticidal action.

Example B-19

Action against *Spodoptera littoralis*

Young soya bean plants are sprayed with an aqueous emulsion spray mixture comprising 400 ppm of active ingredient, then, after the spray coating has dried on, populated with 10 third instar caterpillars of *Spodoptera littoralis,* and then placed in a plastic container. The percentage reduction in population and in feeding damage (% action) is determined 3 days later by comparing the number of dead caterpillars and the feeding damage between the treated and untreated plants. In this test, compounds of Tables 1–4 have good action.

C. Acaricidal action

Example B-20

Action against *Tetranychus urticae*

Young bean plants are populated with a mixed population of *Tetranychus urticae,* sprayed 1 day later with an aqueous emulsion spray mixture comprising 400 ppm of active ingredient, incubated at 25° for 6 days and then evaluated. The percentage reduction in population (% action) is determined by comparing the number of dead eggs, larvae and adults on the treated and untreated plants. Compounds of Tables 1–4 have a considerble acaricidal action.

What is claimed is:

1. An oxime ether of the general formula I

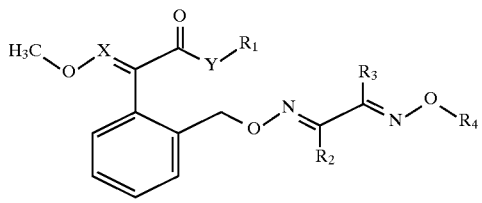

or an isomer or isomer mixture thereof in which
a)
X is an N atom and
Y is an oxygen atom or NH, or
b)
X is CH and
Y is an oxygen atom, in which furthermore $R_1$ is $C_1$–$C_4$ alkyl;

$R_2$ is hydrogen, $C_1$–$C_4$ alkyl, cyclopropyl or cyano;

$R_3$ is, substituted or unsubstituted $C_1$–$C_6$ alkoxycarbonyl, substituted or unsubstituted di($C_1$–$C_6$ alkyl) aminocarbonyl, or substituted or unsubstituted heterocyclylcarbonyl; and $R_4$ is $C_1$–$C_6$ alkyl; $C_1$–$C_6$ haloalkyl having 1 to 5 halogen atoms; $C_1$–$C_4$ alkoxy-$C_1$–$C_2$ alkyl; $C_2$–$C_6$ alkenyl which is unsubstituted or substituted by 1 to 3 halogen atoms; $C_3$–$C_6$ alkynyl; $C_3$–$C_6$ cycloalkyl-$C_1$–$C_4$ alkyl which is unsubstituted or substituted by 1 to 4 halogen atoms, and n assumes a value of 1 or 2.

2. A compound according to claim 1, in which
X is CH or N,
Y is oxygen,
$R_1$ is methyl or ethyl,
$R_2$ is methyl, cyclopropyl or cyano and
$R_3$ and $R_4$ are as defined for formula I.

3. A compound according to claim 1, in which:
X is nitrogen,
Y is NH,
$R_1$ is methyl, ethyl or isopropyl,
$R_2$ is methyl, cyclopropyl or cyano, and
$R_3$ and $R_4$ are as defined for formula I.

4. A compound according to claim 1 in which:
$R_1$=$R_2$ and is methyl,
$R_4$ is $C_1$–$C_6$ alkyl, while
X, Y and $R_3$ are as defined for formula I.

5. A compound according to claim 1 in which:
$R_1$=$R_2$ and is methyl, and
$R_3$, X, Y and $R_4$ are as defined for formula I.

6. A compound according to claim 1, in which:
$R_1$ is substituted or unsubstituted $C_1$–$C_6$ alkoxycarbonyl,
$R_4$ is $C_1$–$C_6$ alkyl, $C_1$–$C_6$ haloalkyl, or $C_3$–$C_6$ cycloalkyl-$C_1$–$C_4$ alkyl which is unsubstituted or substituted by 1 to 4 halogen atoms and
X and Y are as defined for formula I.

7. A compound according to claim 1 in which the X=C double bond is in the E form.

8. A process for the preparation of a compound of claim 1 of the formula I by reacting an oxime of the formula II

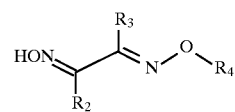

with a benzyl derivative of the general formula III

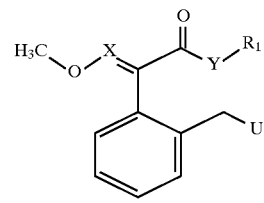

in which $R_1$ to $R_4$, X and Y are as defined for formula I and U is a leaving group.

9. A process according to claim 8, in which the reaction is carried out in the presence of a base in a temperature range of from −20° C. to +80° C.

10. A process for the preparation of a compound of claim 8 of the formula I by reacting an oxime of the formula V

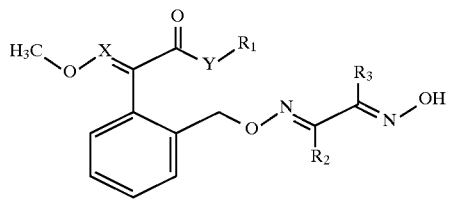

with a compound of the general formula

U-R₄      VI in which $R_1$ to $R_4$, X and Y are as defined for formula I and U is a leaving group.

11. A process according to claim 8, in which the leaving group U is chlorine, bromine, iodine, mesyloxy, benzenesulfonyloxy, nitrobenzenesulfonyloxy or tosyloxy.

12. An intermediate of the formula VII, VIII, IX or X

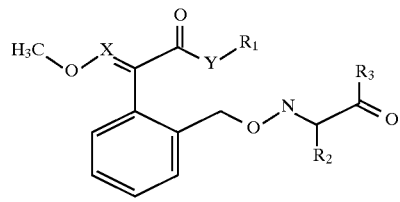

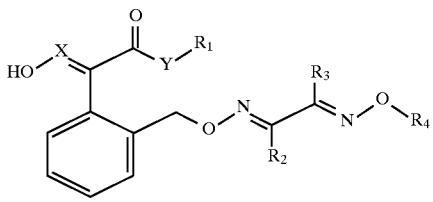

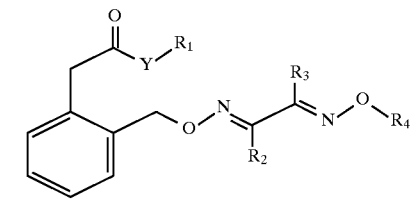

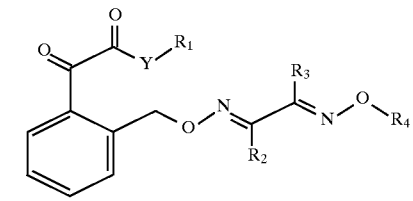

in which $R_1$ to $R_4$, X and Y are as defined for formula I in claim 1.

13. A microbicidal composition which comprises, as active ingredient, at least one compound of the formula I according to claim 1 together with a suitable carrier and, if desired, a surface-active auxiliary.

14. A process for the preparation of a composition according to claim 13 by intimately mixing and/or grinding the active ingredient with a carrier and, if desired, a surface-active auxiliary.

15. A method of controlling plant diseases and of preventing attack by microorganisms by applying a compound of the formula I according to claim 1 to the plant, parts thereof or the locus of its growth.

16. A process for the preparation of compounds of the formula I, which comprises reacting a phenylacetic acid derivative of the formula IX

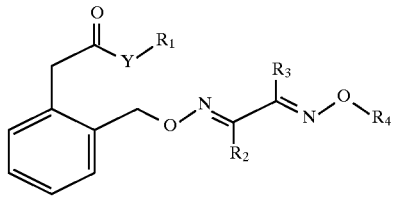

in which Y and $R_1$ to $R_4$ are as defined for formula I in claim 1 with a formate in the presence of a base if a product in which X=CH is to be obtained, or with nitrous acid or a nitrite in the presence of a base if a product in which X=N is to be obtained, in each case with the formation of an enol or oxime derivative of the formula VIII

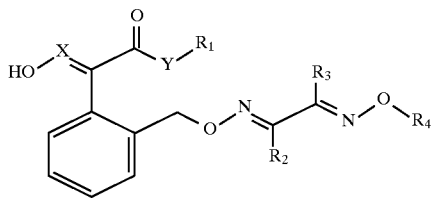

followed by methylation with a methylating agent.

17. An intermediate of the formula II

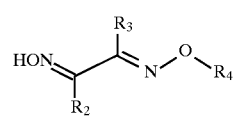

in which $R_2$, $R_3$ and $R_4$ are as defined for formula in claim 1.

18. A compound according to claim 17, in which $R_2$ and $R_4$ are methyl.

* * * * *